(12) United States Patent
Prud'homme et al.

(10) Patent No.: US 9,943,490 B2
(45) Date of Patent: Apr. 17, 2018

(54) COMPOSITE FLASH-PRECIPITATED NANOPARTICLES

(75) Inventors: Robert K. Prud'homme, Lawrenceville, NJ (US); Marian Gindy, Haledon, NJ (US); Ying Liu, Chicago, IL (US)

(73) Assignee: The Trustees of Princeton University, Princeton, NJ (US)

( * ) Notice: Subject to any disclaimer, the term of this patent is extended or adjusted under 35 U.S.C. 154(b) by 1585 days.

(21) Appl. No.: 12/265,206

(22) Filed: Nov. 5, 2008

(65) Prior Publication Data
US 2010/0330368 A1    Dec. 30, 2010

(51) Int. Cl.
| | |
|---|---|
| *B05D 7/00* | (2006.01) |
| *A61K 9/51* | (2006.01) |
| *A61K 49/00* | (2006.01) |
| *A61K 49/18* | (2006.01) |

(52) U.S. Cl.
CPC ........ *A61K 9/5153* (2013.01); *A61K 49/0019* (2013.01); *A61K 49/0065* (2013.01); *A61K 49/0093* (2013.01); *A61K 49/1857* (2013.01); *Y10T 428/2991* (2015.01)

(58) Field of Classification Search
CPC .................................................. A61K 9/5153
USPC ........................................................ 427/212
See application file for complete search history.

(56) References Cited

U.S. PATENT DOCUMENTS

| | | | |
|---|---|---|---|
| 3,970,628 A * | 7/1976 | Connelly et al. ............. | 523/411 |
| 4,684,516 A * | 8/1987 | Bhutani ........................ | 424/469 |
| 5,348,800 A | 9/1994 | Moro et al. | |
| 5,427,767 A | 6/1995 | Kresse et al. | |
| 5,935,889 A * | 8/1999 | Murrell et al. ................... | 502/9 |
| 6,017,948 A | 1/2000 | Rubinfeld et al. ............ | 514/449 |
| 6,045,925 A | 4/2000 | Klabunde et al. | |
| 2003/0092029 A1 | 5/2003 | Josephson et al. | |

(Continued)

FOREIGN PATENT DOCUMENTS

WO    WO/2006/014626    2/2006

OTHER PUBLICATIONS

Zhang, Design of Nanoparticles as Drug Carriers for Cancer Therapy, Cancer Genomics and Proteomics 3: 147-158 (2006).*

(Continued)

*Primary Examiner* — Tabatha Penny
(74) *Attorney, Agent, or Firm* — Medlen & Carroll, LLP

(57) ABSTRACT

The invention described herein relates to sterically stabilized colloidal constructs comprising preformed colloidal particles encapsulated within a polymeric shell. The constructs, which are controllably sized, are nanoparticles comprising hydrophobic elements, electrostatically charged particles with hydrophobic surfaces, hydrophobic inorganic nanostructures, and amphiphilic copolymers with hydrophobic domains and hydrophilic domains. The constructs are made by a process that allows for the simultaneous encapsulation of a preformed colloidal agent as well as a dissolved hydrophobic active within the core of the polymeric nanoparticle. Among the actives incorporated in various embodiments are organic fluorescent dyes, metal nanostructures and superparamagnetic materials for use in combined fluorescence, optical and magnetic resonance imaging applications, and hydrophobic drugs for therapeutic applications.

15 Claims, 18 Drawing Sheets

(56) References Cited

U.S. PATENT DOCUMENTS

| | | | |
|---|---|---|---|
| 2003/0157143 A1* | 8/2003 | Klein | 424/423 |
| 2004/0091546 A1* | 5/2004 | Johnson et al. | 424/501 |
| 2005/0031682 A1* | 2/2005 | Cucala Escoi et al. | 424/464 |
| 2009/0074674 A1 | 3/2009 | Katti et al. | |
| 2010/0297019 A1 | 11/2010 | Lanza et al. | |

OTHER PUBLICATIONS

U.S. Appl. No. 60/951,113, filed Jul. 20, 2007, Schwartz, J.

Adams, M. L. et al. (2003) Amphiphilic block copolymers for drug delivery, *Journal of Pharmaceutical Sciences* 92(7), 1343-1355.

Ai, H. et al. (2005) Magnetite-Loaded Polymeric Micelles as Ultrasensitive Magnetic-Resonance Probes, *Advanced Materials* 17(16), 1949-1952.

Allen, C. et al. (1999) Nano-engineering block copolymer aggregates for drug delivery, *Colloids and Surfaces B: Biointerfaces* 16(1-4), 3-27.

Arshady, R. (1991) Preparation of biodegradable microspheres and microcapsules: 2. Polyactides and related polyesters, *Journal of Controlled Release* 17(1), 1-21.

Azzam, T. and Eisenberg, A. (2006) Monolayer-Protected Gold Nanoparticles by the Self-Assembly of Micellar Poly(ethylene oxide)-b-Poly(ϵ-caprolactone) Block Copolymer, *Langmuir* 23(4), 2126-2132.

Babar Collaboration et al. (2007) Observation of CP Violation in $B \rightarrow \eta' K^0$ Decays, *Physical Review Letters* 98(3), 031801.

Bjørnerud, A. and Johansson, L. (2004) The utility of superparamagnetic contrast agents in MRI: theoretical consideration and applications in the cardiovascular system, *NMR in Biomedicine* 17(7), 465-477.

Bohren, C. F. and Huffman, D. R. (1983) *Absorption and Scattering of Light by Small Particles*, John Wiley, New York.*.

Brick, M. C. et al. (2003) Formation of Colloidal Dispersions of Organic Materials in Aqueous Media by Solvent Shifting, *Langmuir* 19(16), 6367-6380.

Brust, M. et al. (1994) Synthesis of thiol-derivatised gold nanoparticles in a two-phase Liquid-Liquid system, *Journal of the Chemical Society, Chemical Communications*(7).

Bulte, J. W. M. and Kraitchman, D. L. (2004) Iron oxide MR contrast agents for molecular and cellular imaging, *NMR in Biomedicine* 17(7), 484-499.

Butterworth, M. D. et al. (2001) Preparation of ultrafine silica- and PEG-coated magnetite particles, *Colloids and Surfaces A: Physicochemical and Engineering Aspects* 179(1), 93-102.

Davidson, R. (1980) *Handbook of Water-Soluble Gums and Resins*, McGraw-Hill, New York.*.

Discher, D. E. and Eisenberg, A. (2002) Polymer Vesicles, *Science* 297(5583), 967-973.

Duncan, R. and Sat, Y. N. (1998) Tumour targeting by enhanced permeability and retention (EPR) effect, *Annals of Oncology* 9, 39.

Fahmy, T. et al. (2007) Nanosystems for simultaneous imaging and drug delivery to T cells, *The AAPS Journal* 9(2), E171-E180.

Fennel-Evans. (1999) in *Advances in Interfacial Engineering Series* 2nd ed., pp. 417-424.

Gupta, A. K. and Curtis, A. S. G. (2004) Lactoferrin and ceruloplasmin derivatized superparamagnetic iron oxide nanoparticles for targeting cell surface receptors, *Biomaterials* 25(15), 3029-3040.

Gupta, A. K. and Gupta, M. (2005) Synthesis and surface engineering of iron oxide nanoparticles for biomedical applications, *Biomaterials* 26(18), 3995-4021.

Hainfeld, J. F. et al. (2006) Gold nanoparticles: a new X-ray contrast agent, *British Journal of Radiology* 79(939), 248-253.

Holland, S. J. et al. (1986) Polymers for biodegradable medical devices. 1. The potential of polyesters as controlled macromolecular release systems, *Journal of Controlled Release* 4(3), 155-180.

Ilium, L. and Davids, S. S., (Eds.) (1987) *Polymers in Controlled Drug Delivery*, Bristol, U.K., Wright.*.

Johnson, B. K. (2003) Ph.D. Thesis: Flash Nanoprecipitation of Organic Actives Via Confined Micromixing and Block Copolymer Stabilization vol. II, in *Department of Chemical Engineering*, Princeton University, Princeton, N.J.*.

Johnson, B. K. and Prud'homme, R. K. (2003) Chemical processing and micromixing in confined impinging jets, *AIChE Journal* 49(9), 2264-2282.

Johnson, B. K. et al. (2003) Flash NanoPrecipitation of Organic Actives and Block Copolymers using a Confined Impinging Jets Mixer, *Australian Journal of Chemistry* 56(10), 1021-1024.

Kim, B.-S. and Taton, T. A. (2006) Multicomponent Nanoparticles via Self-Assembly with Cross-Linked Block Copolymer Surfactants, *Langmuir* 23(4), 2198-2202.

Kim, S. (1993) Liposomes as carriers of cancer chemotherapy. Current status and future prospects, *Drugs* 46(4), 618-638.

Kwon, G. S. and Kataoka, K. (1995) Block copolymer micelles as long-circulating drug vehicles, *Advanced Drug Delivery Reviews* 16(2-3), 295-309.

Kwon, S. (1998) Diblock copolymer nanoparticles for drug delivery, *Critical reviews in therapeutic drug carrier systems* 15(5), 481-512.

Lavasanifar, A. et al. (2002) Poly(ethylene oxide)-block-poly(1-amino acid) micelles for drug delivery, *Advanced Drug Delivery Reviews* 54(2), 169-190.

Link, S. and El-Sayed, M. A. (2000) Shape and size dependence of radiative, non-radiative and photothermal properties of gold nanocrystals, *International Reviews in Physical Chemistry* 19(3), 409-453.

Liu et al. (2007) *Chemical Engineering Research*.*.

Liu, Y. et al. (2007) Nanomedicine for drug delivery and imaging: A promising avenue for cancer therapy and diagnosis using targeted functional nanoparticles, *International Journal of Cancer* 120(12), 2527-2537.

Loo, C. et al. (2004) Nanoshell-Enabled Photonics-Based Imaging and Therapy of Cancer, *Techology in Cancer Research & Treatment* 3(1), 33-40.

Luo, L. et al. (2002) Cellular Internalization of Poly(ethylene oxide)-b-poly(ϵ-caprolactone) Diblock Copolymer Micelles, *Bioconjugate Chemistry* 13(6), 1259-1265.

Michalet, X. et al. (2005) Quantum Dots for Live Cells, In Vivo Imaging, and Diagnostics, *Science* 307(5709), 538-544.

Mornet, S. et al. (2004) Magnetic nanoparticle design for medical diagnosis and therapy, *Journal of Materials Chemistry* 14(14).

Nasongkla, N. et al. (2006) Multifunctional Polymeric Micelles as Cancer-Targeted, MRI-Ultrasensitive Drug Delivery Systems, *Nano Letters* 6(11), 2427-2430.

O'Reilly, R. K. et al. (2006) Facile syntheses of surface-functionalized micelles and shell cross-linked nanoparticles, *Journal of Polymer Science Part A: Polymer Chemistry* 44(17), 5203-5217.

Paciotti, G. F. et al. (2006) Colloidal gold nanoparticles: a novel nanoparticle platform for developing multifunctional tumor-targeted drug delivery vectors, *Drug Development Research* 67(1), 47-54.

Paciotti, G. F. et al. (2004) Colloidal Gold: A Novel Nanoparticle Vector for Tumor Directed Drug Delivery, *Drug Delivery* 11(3), 169-183.

Pankhurst, Q. A. et al. (2003) Applications of magnetic nanoparticles in biomedicine, *Journal of Physics D: Applied Physics* 36, R167-R181.

Pitt, C. G. (1990) The controlled parenteral delivery of polypeptides and proteins, *International Journal of Pharmaceutics* 59(3), 173-196.

Portney, N. and Ozkan, M. (2006) Nano-oncology: drug delivery, imaging, and sensing, *Analytical and Bioanalytical Chemistry* 384(3), 620-630.

Savić, R. et al. (2003) Micellar Nanocontainers Distribute to Defined Cytoplasmic Organelles, *Science* 300(5619), 615-618.

Shibasaki, Y. et al. (2000) Activated Monomer Cationic Polymerization of Lactones and the Application to Well-Defined Block Copolymer Synthesis with Seven-Membered Cyclic Carbonate, *Macromolecules* 33(12), 4316-4320.

(56) References Cited

OTHER PUBLICATIONS

Shuai, X. et al. (2004) Micellar carriers based on block copolymers of poly(e-caprolactone) and poly(ethylene glycol) for doxorubicin delivery, *Journal of Controlled Release* 98(3), 415-426.

Shuai, X. et al. (2003) Novel Biodegradable Ternary Copolymers hy-PEI-g-PCL-b-PEG: Synthesis, Characterization, and Potential as Efficient Nonviral Gene Delivery Vectors, *Macromolecules* 36(15), 5751-5759.

Soo, P. L. et al. (2007) Gold-Labeled Block Copolymer Micelles Reveal Gold Aggregates at Multiple Subcellular Sites, *Langmuir* 23(9), 4830-4836.

Soppimath, K. S. et al. (2001) Biodegradable polymeric nanoparticles as drug delivery devices, *Journal of Controlled Release* 70(1-2), 1-20.

Terrill, R. H. et al. (1995) Monolayers in Three Dimensions: NMR, SAXS, Thermal, and Electron Hopping Studies of Alkanethiol Stabilized Gold Clusters, *Journal of the American Chemical Society* 117(50), 12537-12548.

Torquato, S. et al. (2000) Is Random Close Packing of Spheres Well Defined?, *Physical Review Letters* 84(10), 2064-2067.

Wang, Y.-X. et al. (2001) [Without Title], *European Radiology* 11(11), 2319-2331.

West, J. L. and Halas, N. J. (2003) Engineered Nanomaterials for Biophotonics Applications: Improving Sensing, Imaging, and Therapeutics, *Annual Review of Biomedical Engineering* 5(1), 285-292.

Yang, J. et al. (2007) Antibody conjugated magnetic PLGA nanoparticles for diagnosis and treatment of breast cancer, *Journal of Materials Chemistry* 17, 2695-2699.

Yu, S. and Chow, G. M. (2004) Carboxyl group ($-CO_2H$) functionalized ferrimagnetic iron oxide nanoparticles for potential bio-applications, *Journal of Materials Chemistry* 14(18), 2781-2786.

Zhang, Y. et al. (2002) Surface modification of superparamagnetic magnetite nanoparticles and their intracellular uptake, *Biomaterials* 23(7), 1553-1561.

Zhou, J. et al. (2006) Sub-cellular accumulation of magnetic nanoparticles in breast tumors and metastases, *Biomaterials* 27(9), 2001-2008.

\* cited by examiner

COMPOSITE FLASH-PRECIPITATED NANOPARTICLES

GOVERNMENT RIGHTS IN THIS INVENTION

This invention was made with government support under Grant No. CMS0609049 awarded by the National Science Foundation. The government has certain rights in the invention.

FIELD

The invention relates to the field of nanotechnology. In particular, the invention is embodied in a hydrodynamic process for manufacturing a hydrophilic carrier, preferably less than 1000 nanometers in size, that encapsulates hydrophobic agents or electrostatically charged agents with hydrophobic surfaces, including pharmaceuticals, organic imaging agents or fluorescent dyes, and solid inorganic nanostructures.

BACKGROUND

Nanoparticles have become increasingly important in the development of new materials for enhanced drug delivery and imaging applications (Adams, M. L. et al., *J. Pharmaceutical Sciences* 2003, 92:1343-1355; Portney et al., *Analytical and Bioanalytical Chemistry* 2006, 384:620-630). Drug carriers such as liposomal (Kim, S. *Drugs* 1993, 46:618-638), polymeric vesicle (Discher et al., *Science* 2002, 297, 967-973) and micellar dispersions (Allen et al., *Colloids and Surfaces B—Biointerfaces* 1999, 16:3-27; Kwon, *Critical Reviews in Therapeutic Drug Carrier Systems* 1998, 15:481-512) consisting of particles 50-400 nm in diameter have shown great promise, for example, in the formulation of anticancer therapeutics that would be highly insoluble in aqueous media absent their incorporation into a carrier. Such carriers, besides affording more potent drug delivery, also provide opportunities for selective tumor targeting. More recently, inorganic nanoparticles, including quantum dots (Michalet et al, *Science* 2005, 307:538-544) gold nanospheres (West et al., *Annual Review of Biomedical Engineering* 2003, 5:285-292), nanoshells (Loo et al. *Cancer Research and Treatment* 2004, 3:33-40), and superparamagnetic metals (Mornet et al., *Journal of Materials Chemistry* 2004, 14:2161-2175) have been explored for nanoparticle-based biomedical functions, such as tagging, medical imaging, sensing, and separation.

Despite extensive innovation over the last decade, there remains a need for integrated, easily adaptable drug delivery and imaging modalities, especially those for the delivery and monitoring of highly toxic compounds in vivo. Polymeric nanoparticles in particular are a versatile medium for this purpose, due to their enhanced drug loading capacity, biological stability, and extended in vivo circulation times (Kwon et al., *Advanced Drug Delivery Reviews* 1995, 16:295-309).

Polymeric nanoparticles that carry drugs and other agents encapsulated in their cores have evolved. Initially, research efforts focused on combining polymeric carriers of drugs with organic fluorescent dyes for particle visualization, without regard to the "encapsulation" of either the drug or the dye. Fluorescent nanoparticless have been prepared by binding water-soluble fluorophores to the surfaces of pre-formed nanoparticles (O'Reilly et al., *Journal of Polymer Science Part A—Polymer Chemistry* 2006, 44: 5203-5217) or, more commonly, by chemically tethering a fluorescent dye to the hydrophobic terminus of an amphiphilic block copolymer and then permitting the polymer to self-assemble into a particle (Luo, et al., *Bioconjugate Chemistry* 2002, 13:1259-1265). Organic dyes and fluorophores, however, require direct visualization, and so are generally practical only for in vitro applications such as nanoparticle cellular uptake and localization studies (Savic et al., *Science* 2003, 300:615-618).

Nanoparticles having a metallic core that adds contrast to images acquired by magnetic resonance imaging, for example, or computed X-ray tomography are more suitable for in vivo biomedical applications (Bulte et al., *NMR in Biomedicine* 2004, 2004, 17: 484-499; Hainfeld et al., *British Journal of Radiology* 2006, 79:248-253). Typically, however, they are incompatible with body fluids because their surfaces are hydrophobic and they may also be incompatible because of toxicity. A number of coating strategies have been used to address these issues (Azzam et al., *Langmuir* 2007, 23:2126-2132; Kim et al., *Langmuir* 2007, 23: 2198-2202; Butterworth et al., *Colloids and Surfaces A—Physicochemical and Engineering Aspects* 2001, 179: 93-102; Gupta et al., *Biomaterials* 2005, 26: 3995-4021; Soo et al., *Langmuir* 2007, 23:4830-4836). Researchers have also functionalized the surfaces of such inorganic nanoparticles with receptor-specific peptides or protein ligands, allowing for targeted localization of the imaging particles (Paciotti et al., *Drug Development Research* 2006, 67:47-54; Zhang et al., *Biomaterials* 2002, 23:1553-1561; Zhou, et al., *Biomaterials* 2006, 27:2001-2008). Also, ligands (optionally together with drugs) can be covalently attached to the coating material instead of to the inorganic nanoparticle itself (Paciotti et al., *Drug Delivery* 2004, 11:169-183; Yu et al., *Journal of Materials Chemistry* 2004, 14: 2781-2786; Gupta et al., *Biomaterials* 2004, 25:3029-3040). Since the coating material is advantageously hydrophilic, however, the strategy of attaching hydrophobic moieties (e.g., drugs) to it is generally not practical.

SUMMARY

In one embodiment, the present invention contemplates a process for manufacturing composite nanoparticles, the process comprising:
  a. providing an organic compound dissolved in a solvent,
  b. providing an inorganic nanoparticle dispersed in the same solvent,
  c. providing an amphiphilic polymer dissolved in the same solvent, and
  d. mixing the solvent mixture with an anti-solvent such that a composite nanoparticle forms, the composite nanoparticle comprising the organic compound, the inorganic nanoparticle and the amphiphilic polymer.

In preferred embodiments, the organic compound is hydrophobic and insoluble in water, the inorganic nanoparticle is hydrophobic, and the solvent is a water-miscible organic solvent such as tetrahydrofuran, dimethyl sulfoxide, or ethanol.

In some embodiments, a first solvent in which the nanoparticle is dispersed, a second solvent in which the organic compound is dissolved and a third solvent in which the polymer is dissolved are provided and mixed with the anti-solvent under conditions such that the composite nanopraticle forms.

The inorganic nanoparticle may be surface-modified prior to step d above. It may also be functionalized to give the nanoparticle a hydrophilic surface. The organic compound may be electrostatically charged prior to step d, as may the inorganic nanoparticle.

In preferred embodiments, the invention provides a dispersion of composite nanoparticles that does not flocculate in an aqueous solvent.

The amphiphilic polymer may be selected from the group consisting of any copolymer, block copolymer, graft copolymer, comb-graft copolymer, and random copolymer that contains both hydrophobic and hydrophilic regions within the same copolymer.

The inorganic nanoparticle may be selected from the group consisting of magnetic, paramagnetic and superparamagnetic metals, and oxides thereof, or from the group consisting of gold, palladium and oxides thereof, or it may be a quantum dot.

In an embodiment especially preferred for use in magnetic resonance imaging, the inorganic nanoparticle comprises an iron oxide. In a most preferred embodiment, the iron oxide comprises $CoFe_2O_4$. In some embodiments, the iron oxide is a nanocrystal.

Preferably, the organic compound and the inorganic nanoparticle are encapsulated in a hydrophobic core region of the composite nanoparticle, and a hydrophilic shell surrounds the core. Encapsulated compounds and particles may be stabilized therein by means of steric hindrance, electrostatic charge stabilization or a combination thereof.

Some embodiments of the invention comprise a composite nanoparticle, said nanoparticle comprising an organic compound, preferably hydrophobic, an inorganic nanoparticle, which may be metallic or non-metallic, and an amphiphilic copolymer. The composite nanoparticle may comprise a pharmaceutical composition, said pharmaceutical composition comprising a pharmaceutically acceptable carrier or diluent.

In some embodiments, the inorganic nanoparticle is an imaging contrast agent which may be selected, without limitation, from the group of metals consisting of Gd(III), Mn(II), Mn(III), Cr(II), Cr(III), Cu(II), Fe(III), Pr(III), Nd(III), Sm(III), Tb(III), Yb(III), Ho(III), Eu(II), Eu(III), Er(III), Indium (In), Technetium (Tc), and Barium or from the group of non-metals consisting of Iodine (I), Bromine, Fluorescein, Carboxyfluorescein and Calcein.

The composite nanoparticle may further comprise a targeting agent, which may be anchored on the external surface of the hydrophilic shell. In some embodiments, the encapsulated organic compound or the inorganic nanoparticle are releasable from the composite nanoparticle. In some embodiments, the released compound, the released nanoparticle, or both, have targeting properties.

In some embodiments, the composite nanoparticle may further comprise a therapeutic agent embodied in the organic compound, the inorganic nanoparticle, the targeting agent or the amphiphilic copolymer of the composite nanoparticle.

In some embodiments, the invention provides a method of in vivo imaging of a site of disease in a subject, including without limitation a tumor, atherosclerotic plaque, an anatomic anomaly, or a benign lesion, the method comprising administering to the subject the composite nanoparticle.

In some embodiments, the invention provides a method of determining the distribution of the therapeutic agent in a subject being treated with the therapeutic agent as a function of the distribution of an image generated by the inorganic particle. In some embodiments, the image is an MRI image. In other embodiments, the image may be an X-ray image, a scintillographic image or an optical image.

In some embodiments, the composite nanoparticle, which is preferably less than about 500 nm in mean intensity-average diameter, has a dispersity index of less than about 0.3, and preferably less than about 0.25. In some embodiments, the inorganic nanoparticles comprise at least 1% of the weight of the composite nanoparticle, and may comprise up to 50%.

DETAILED DESCRIPTION

Figure 1:
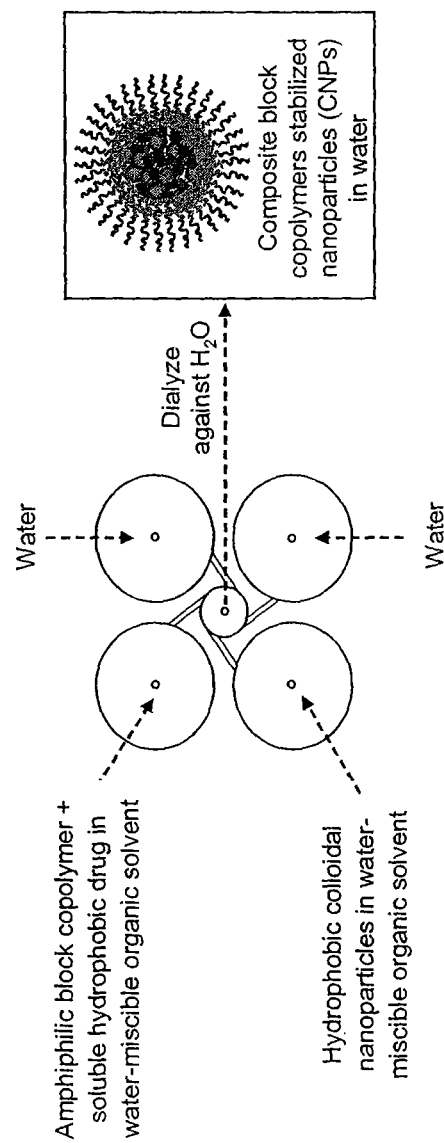
FIG. 1 is a schematic of a process for preparing multi-component ("composite") nanoparticles by flash nanoprecipitation in a multi-inlet vortex mixer, and a product thereof.

One way of delivering hydrophobic materials in vivo would be to encapsulate hydrophobic moieties within a polymeric carrier that is externally hydrophilic. This has proven to be a difficult problem when one seeks to capture inorganic nanostructured solids in such a carrier, especially if the nanostructures are to be co-encapsulated with hydrophobic organic compounds.

Although the Applicants will not be bound by any theory of how embodiments of the instant invention work, it is widely understood that, in contrast to molecules and the atoms of ionic crystals such as sodium chloride that dissolve in dilute solution and move about independently in (dilute) solution, nanostructures do not dissolve in a solvent as individual atoms or molecules. The atoms of a nanostructure are organized as a solid at the core. Solvents do not disrupt the core. Thus, nanoparticles disperse in solvents as particles, not as individual atoms or molecules. In part because of this, they attract one another readily, and aggregate readily.

To make a nanoparticulate carrier that is a composite of hydrophobic organic compounds and inorganic nanostructures, which carrier is to remain dispersed in an aqueous solvent, one is faced with finding a way of (1) stabilizing dispersions of nanostructures in a local environment that is loaded with hydrophobic organic and inorganic agents (Liu et al., *International Journal of Cancer* 2007, 120: 2527-2537; Fahmy et al., *The AAPS Journal* 2007, 9:E171-E180) and (2) stabilizing a population of the carriers as a dispersion in an aqueous solvent, bearing in mind that the carriers are themselves nanoparticles susceptible to aggregation.

The polymeric component of such a carrier suggests the possibility of stabilizing dispersions within the carrier sterically; that is, by utilizing the polymer to build barriers between nanoparticles in the dispersions. The advantages of such delivery systems, viz., high drug-loading capacity, reduced toxicity, protection of carried agents from the surrounding environment, targeting, localization and monitoring, and the possibility of tailoring the system's drug release kinetics (Kwon et al., 1998; Soppimath et al., *Journal of Controlled Release* 2001 70:1-20) are appreciated, but only a limited literature on the successful preparation of hybrid organic-inorganic nanoparticle formulations exists. For example, Gao and coworkers (Nasongkla et al., Nano Letters 2006 6:2427-2430) have described the preparation of composite poly(ethylene glycol)-block-poly(D,L-lactide) micelles encapsulating chemotherapeutic doxorubicin and superparamagnetic iron oxide nanoparticles. More recently, the successful preparation of antibody-conjugated poly(D, L-lactide-co-glycolide) nanoparticles incorporating doxorubicin and magnetic iron nanocrystals was reported by Yang et al. (*Journal of Materials Chemistry* 2007, Advance Article). In both cases, enhanced cancer cell affinity and improved magnetic resonance signals were reported in vitro. Unfortunately, the preparative techniques that were employed, namely solvent evaporation and emulsification processes, suffer from several disadvantages. First, they require the use of stabilizing surfactants and numerous purification stages to achieve only a low yield of uniformly sized nanoparticles. Additionally, hydrophobic components are relatively insoluble within the particles, so they cannot host hydrophobic components at high capacity (Shuai et al., *Journal of Controlled Release* 2004, 98:415-426). Lastly, these preparative processes do not allow the artisan to independently specify the amounts or kinds of individual components that the final nanoparticle will carry. Constraining the artisan are the unequal solubilities and miscibilities among the hydrophobic components, any nanostructures to be incorporated, and the hydrophobic domains of the stabilizing polymers. Furthermore, the processes do not ensure uniform distribution of actives within the nanoparticulate carriers.

In its various embodiments, the present invention provides composite nanoparticles that carry organic and inorganic materials in nanoparticulate "capsules" whose outer surfaces are compatible with aqueous solvents and remain homogeneously disperse in them.

In describing the embodiments, the following meanings attach to the terms employed. Unless otherwise noted, all terms of art, notations, scientific terms or other terminology have the meaning commonly understood by persons of ordinary skill in the art to which the embodiments of the invention pertain, but may be defined herein for clarity or convenience.

As used herein, "a" or "an" means "at least one" or "one or more."

The term "active agent" or "agent" refers herein to any chemical moiety or substance that has a desired behavior or activity. Non-limiting examples include elements, inorganic or organic ions, molecules, complexes, particles, crystals and radionuclides that may be "active" (without limitation) as pharmaceuticals, as contrast agents in imaging applications, as colorants, flavors, and fragrances, as sources or absorbers of energy, as linking or binding agents, or as toxins.

As used herein, a "nanoparticle" is any object of a size less than about 1 micron. It is not necessary that such a particle conform to this limit in all of its dimensions. Indeed, it is not even necessary that such a particle have dimensions in the conventional sense. Quantum dots, for example, may be referred to as "nanoparticles" herein. An "inorganic nanoparticle" as the term is used herein, generally refers to a particle comprising a metallic element, and an "organic nanoparticle" generally refers to a particle comprising a polymer (nanoparticles structured from elemental carbon are generally not regarded as "organic"). Particles comprising a polymer and at least one other material may be defined as "composite nanoparticles," but the term as used herein typically refers to nanoparticles constructed of a polymer, an inorganic nanoparticle, and another component that is neither a polymer nor an inorganic nanoparticle.

As used herein, "dissolved" or "molecularly dissolved" molecules or atoms are homogenously distributed in a solvent and move about therein randomly and largely independently of one another. A substance that is "insoluble in an aqueous medium" dissolves in solutions that are physiologically relevant with respect to ionic strength, osmolality and pH only to the extent of 0.05 mg/ml or less. A solution that is "insoluble in pure water" dissolves in pure water only to the extent of 0.05 mg/ml or less. The criterion for "soluble" on the other hand is 1.0 mg/ml or more.

A "colloid" as used herein is analogous to a solution: both are systems of molecules, atoms or particles in a solvent. The particles of a colloidal system, however, because of their size (nanometers) or the distance between them (also nanometers), attract one another with sufficient force to make them tend to aggregate even when the only means of transport for the particles is diffusion (the "diffusion-limited regime"). As used herein, the term "colloidal particles" refers to particles capable of forming a colloid. Although a "colloidal particle" is not itself a colloid but only a constituent of a colloid, the term "colloid" is often used to denote particles itself Thus, when the context so admits, the term "colloid" may refer herein to a particle. The term "colloidal dispersion" herein distinguishes colloids from true solutions on the one hand and from "suspensions" of larger particles on the other hand. In the latter, the particles tend to "settle out" like sand stirred in water. A colloid, in contrast, tends to "flocculate" when large aggregates of particles form in the dispersion. The terms "colloidal dispersion" and "colloidal suspension" are often used interchangeably and may be so used herein. Instead of being "dissolved" in a solvent, the particles in a colloidal dispersion are said to be "solubilized" in the solvent. The solvent may be referred to as a "continuous phase" and, more colloquially, as the "surrounding environment."

As used herein, the term "emulsion" is a dispersion of liquid droplets or liquid crystals in a liquid, wherein the droplets or crystals are generally larger than the particles in a colloidal system.

As used herein, a "polydisperse" colloid comprises particles that range in size. In a "narrowly polydisperse" colloid, the range is small.

As used herein, "organic compounds" encompass the entire domain of organic chemistry. Unless the context admits otherwise, however, organic compounds are generally distinguished herein from polymers.

As used herein, a "hydrophobic moiety" is insoluble in aqueous solutions as defined above. The "moiety" may be, without limitation, a small molecule, a nanoparticle, a polymer or a region of a polymer. Colloidal particles may be hydrophobic or hydrophilic. Colloids (i.e., colloidal dispersions) may also be referred to herein as "hydrophobic" or "hydrophilic." A colloidal dispersion comprising an aqueous continuous phase with hydrophobic particles dispersed therein is referred to as a hydrophobic colloid or hydrophobic dispersion. Hydrophobic dispersions are thermodynamically unstable if the dispersion medium (or continuous phase) is aqueous. Conversely, a hydrophilic dispersion may be unstable if the dispersion medium is a non-polar solvent. Amphiphilic stabilizers may be incorporated into such dispersions to counter the instability. As used herein, an "amphiphilic stabilizer" is a compound having a molecular weight greater than about 500 grams/mole that has a hydrophilic region or domain and a hydrophobic region or domain. Preferably, the molecular weight is greater than about 1,000, or 1,500 or 2,000, and may be much higher, e.g., 25,000 or 50,000 grams/mole. Preferably, an amphiphilic stabilizer is a polymer, and more preferably a polymer or polymer system that provides both hydrophobic and hydrophilic domains to the colloid Block copolymers, graft copolymers, comb-graft copolymers, and random copolymers that contain both hydrophobic and hydrophilic regions within the same copolymer are useful.

As used herein, the term "mixing" may refer, when the context so admits, to "micromixing," which has a particular meaning herein as set forth in detail below.

Conventionally, the term "anti-solvent" relates to a solvent which, when admixed with a solution comprising a second solvent, tends to cause the solute in the second solvent to precipitate. When admixed with a colloid, an anti-solvent may cause flocculation, in analogy with precipitation of a solute, but admixing a solvent containing dispersed nanoparticles and dissolved organic moieties with an anti-solvent may cause, instead of precipitation or flocculation, the self-assembly of particles of a different construction, as is described herein. The latter are distinguished herein from the "pre-formed" or "pre-existing" nanoparticles that may be incorporated therein. For clarity, the usual implication that an anti-solvent precipitates a solute, does not obtain herein.

As used herein, the term "surface-modification" refers to a process wherein reactive chemical groups on a surface, in particular the surface of a nanoparticle, are added to, removed from, or altered. The modified surface is sometimes referred to as having been "functionalized."

As used herein, the term "surface-modification" refers to a process wherein reactive chemical groups on a surface, in particular the surface of a nanoparticle, are added to, removed from, or altered. The modified surface is sometimes referred to as having been "functionalized."

As used herein, the term "encapsulation" relates to protecting constituents of the composite nanoparticle embodiments of the invention from reacting with or diffusing into the medium in which the composite nanoparticle is dispersed. Any such constituent is said to be "incorporated" in the nanoparticle as a "carried agent." No distinct structural element is required to confer the protecting function. Similarly, the term "shell" relates herein to the protective function of a shell and not to any particular structure. The shell of a nanoparticle may confer hydrophilicity or hydrophobicity on its nanoparticle, may be surface-modified, and may have adsorbed, bound or otherwise anchored to it, without limitation, molecules that interact (bind, react with, complex with) specifically with desired sites in or on materials, including without limitation natural or synthetic fibers, and plant or animal cells. Such molecules can include, without limitation, antibodies, receptor ligands, and any other means of linking a nanoparticle to a site of interest. Nanoparticles so modified are said to be "targeted" to the desired site, and the antibody, ligand, etc. may be referred to herein as a "homing" molecule or agent. The shell may be used to affix a "tag" (viz., a means that emits a detectable signal) to a nanoparticle to monitor the whereabouts, the integrity, etc. of the nanoparticle. Alternatively, such a tag may be incorporated into the nanoparticle. As used herein, a "capsule" or "shell" may also have the property of allowing encapsulated materials carried in the nanoparticle to be controllably released therefrom.

The term "core," as it relates to the nanoparticles referred to herein, is a solid-state material which, in its nanoparticle, is not susceptible to dissolution in the nanoparticle's dispersion medium.

The term "kinematic viscosity" as used herein refers to the tendency of a fluid to resist flowing (viscosity), factored by the fluid's density. It is the viscosity of a fluid divided by its density.

As used herein, the term "surface plasmon resonance" relates to a phenomenon detectable on metallic surfaces. The "free" electrons that are characteristic of metals move about within the metal and also on its surface (as a so-called "plasma" or "electron gas"). Electromagnetic surface waves attend the movement. Because they are "quantized," the waves have particle-like properties. The "particles" are called "plasmons." Plasmons can interact with light, changing its behavior in detectable ways. Under appropriate conditions, the interaction is "resonant." That is, a plasmon can absorb the light's energy, producing what is appreciated by the observer as a "shadow." These "shadows" are a manifestation of surface plasmon resonance. The phenomenon may be taken advantage of herein to distinguish metal-containing colloids in nanostructures from monomeric metal.

Certain embodiments of the instant invention relate to magnetic resonance imaging, especially to agents useful for improving the contrast between elements of an image. Accordingly, some basic principles of magnetic resonance imaging are summarized below to provide a better understanding of the utility of these embodiments. The discussion is not intended to limit the scope of the invention in any of its embodiments, especially insofar as any theory may be set forth to explain how the embodiments are thought to work.

Magnetic materials (iron oxides) are classified by their response to an externally applied magnetic field, and can be described as ferromagnetic, paramagnetic and superparamagnetic (Mornet et al. *Journal Materials Chemistry* 2004, 14: 2161-2175; Gupta et al. *Biomaterials* 2005, 26: 3995-4021). A "magnetic material," broadly conceived, is any material that has—or can be made to have—an electron in motion within, on or around it, inasmuch as a moving electron generates a magnetic force field or "moment." Since individual atoms typically have at least one moving electron, they exhibit a magnetic moment or "magnetic dipole," a term that derives from the fact that moments, in addition to having magnitude, also have a direction (or orientation). That is, they are vectors. Ferromagnetic materials are intrinsically magnetic because they comprise atoms bound together in a domain, such that the entire domain becomes a magnetic dipole. Typically, a ferromagnetic material comprises many such domains and the extent of their alignment determines the magnetic strength of the bulk material. A ferromagnetic material that does not appear to be magnetic will become so, permanently, once it has been exposed, even briefly, to an external magnetic field of sufficient force and orientation to align all the domains in the material. A "paramagnetic" material is different in that it becomes magnetic only under the influence of an externally applied field (but may actually increase the force of that field) and rapidly loses its magnetization when the external field is removed.

The magnetic properties of a ferromagnetic material can change markedly when its bulk is reduced from macroscopic to nanometer scaled particles (Mornet et al. *Journal Materials Chemistry* 2004, 14: 2161-2175; Gupta et al. *Biomaterials* 2005, 26: 3995-4021; Pankhurst et al. *J. Physics D—Applied Physics* 2003, 36: R167-R181). Nanometer-sized ferromagnetic particles demonstrate magnetic properties that are characteristic of neither a collection of "independent" atomic dipoles nor a collection of dipole domains. In a bulk ferromagnetic material, magnetic domains can be aligned or "anti-aligned." The transition between the two domains is called a "Block wall." At the nanometer scale, the formation of Block walls becomes thermodynamically unfavorable, leading to the formation of single-domain crystals (Mornet et al. *Journal Materials Chemistry* 2004, 14: 2161-2175; Pankhurst et al. *J. Physics D—Applied Physics* 2003, 36: R167-R181). These single-domain crystals are no longer ferromagnetic, but exhibit superparamagnetism. For each ferromagnetic material, a critical particle size exists below which domain walls cease to exist.

Superparamagnetic crystals, like paramagnetic materials, lose magnetization when deprived of an external field, but in such a field, they exhibit a much higher magnetic moment. The characteristic strong magnetic susceptibility (in comparison to paramagnetic materials) of superparamagnetic particles at this scale is a consequence of the single crystal nature of the material, which permits the entire crystal to align with the applied field.

MRI is based on the nuclear magnetic resonance (NMR) signal of protons in water, lipids, proteins, etc. in tissue, through the combined effect of a strong static magnetic field, $B_0$, and a transverse radiofrequency-field (also a magnetic field, but oscillatory). The counterbalance between the exceedingly small magnetic moment of a single proton (it is convenient to visualize the magnetic moment associated with a proton as a spinning top with a north and south magnetic pole, bearing in mind that the moment of a proton refers to a "field," not a dimensioned structure), and the exceedingly large number of protons present in biological tissue, leads to a measurable effect in the presence of large magnetic fields. For example, for $B_0$=1 Tesla (T), only three of every million proton moments m are effectively aligned parallel to $B_0$. However, there are so many protons available ($6.6 \times 10^{19}/mm^3$ of water) that the effective signal ($2 \times 10^{14}$ proton moments/$mm^3$) is observable (Pankhurst et al. *J. Physics D—Applied Physics* 2003, 36: R167-R181). In a clinical setting, the static field, $B_0$, can be up as high as 4 T, while the radiofrequency-field ("RF") varies between 5-100 MHz (Mornet et al. *Journal Materials Chemistry* 2004, 14: 2161-2175).

The relatively rare aligned proton moments, which spin "straight up" in the static field except for a slight "wobble" (precession) at a characteristic frequency (the "Larmor frequency"), are forced by the RF field to process in resonance with the RF field so that the amplitude of the precession increases (the spinning top "leans" severely). The wobbling magnetic moment is, in effect, an antenna that emits a signal (detectable by MRI machines) when its precession amplitude changes. When the RF field is turned off, the precession of the proton's moment "relaxes" as the static field takes over from the vanishing transverse field. It is important to note that relaxation is the result of two factors, each of which has its own relaxation time or, more precisely, time constant, referred to as "$T_1$" and "$T_2$." The transverse field decays rapidly ($T_2$), whereas the static field reasserts its influence slowly ($T_1$) as stored RF energy dissipates into surrounding tissues, which can be visualized as a "lattice" in which the protons are embedded. The reference to "spin-lattice" relaxation derives from the dissipation of the energy stored in the "spin" of the magnetic moment into the lattice. In contrast, spin energy contributed by the transverse field is "dumped" into the spinning magnetic moment (thus the term "spin-spin" relaxation).

In practice, the time-variant magnetic field (radio frequency transverse field) is applied as a pulsed sequence in a plane perpendicular to $B_0$ and is tuned to the Larmor precession frequency, $\omega_0$, of the proton's moment in order to get the resonance effect. Despite being much weaker than $B_0$, this field has the effect of resonantly exciting the moment's precession into the plane perpendicular to $B_0$, driving a coherent response from the net magnetic moment of the protons in the MRI scanner. After the radio frequency sequence is finished, the net magnetization vector is once again influenced by $B_0$ and tries to realign with it along the longitudinal axis. This relaxation of the coherent response is measured via induced currents in pick-up coils in the scanner, which can enhance the signal by a quality factor of approximately 50-100.

In order to correlate the signal to its spatial origin, at least one of the two fields (i.e. $B_0$ or the radio frequency field) has to vary over space. Relaxation data are collected by a computer which applies a two-dimensional Fourier transform to give the amplitudes of NMR signals and permit reconstruction of a 3-D image. Depending on the sequence parameters, such as the repetition time "TR" (elapsed time between successive radio frequency excitation pulses) and the delay time "TE" ("echo" time, or the time interval between pulse and measurement of the first signal), the desired type of image contrast, $T_1$ or $T_2$, can be obtained. In general, short TRs increase $T_1$ effects, whereas long TRs allow tissues to reach complete longitudinal magnetization, reducing $T_1$ effects. Short TEs minimize $T_2$ effects of tissues whereas long TEs allow the loss of transverse signal, enhancing $T_2$ effects.

Both $T_1$ and $T_2$ can be shortened by the use of paramagnetic and superparamagnetic contrast agents. This effect is quantified in terms of the concentration-independent relaxivities (Bjornerud et al. *NMR in Biomedicine* 2004, 17: 465-477). The efficiency by which a contrast agent can accelerate the rate of relaxation of proton moments in a homogeneous medium is called relaxivity of the agent and is defined by:

$$R_{1,2} = R_{1,2}^0 + r_{1,2} C \quad [1]$$

where $R_1 = 1/T_1$ and $R_2 = 1/T_2$ are the respective $T_1$ and $T_2$ reciprocal relaxation times (unit $s^{-1}$) and C is the contrast agent concentration (unit mM). $R_{1,2}^0$ are the relaxation rates in the absence of contrast agent. The slopes of these curves yield the concentration independent $T_1$ and $T_2$ relaxivities, $r_1$ and $r_2$ (unit $s^{-1}$ $mM^{-1}$), respectively.

In general, there are two classes of MR contrast agents. On the one hand, there are agents that have low $r_2/r_1$ ratios, and therefore generate positive contrast. For example, the moments of protons in proximity to paramagnetic Gd chelates experience a faster $T_1$ relaxation than protons in the absence of such particles. Consequently, differences in agent concentration result in contrast enhancement on $T_1$-weighted images ('positive' contrast). On the other hand, superparamagnetic nanoparticles produce predominantly $T_2$ relaxation effects, corresponding to a high $r_2/r_1$ ratio, which results in signal reduction on $T_2$-weighted images ('negative' contrast). The phenomenon may be described from the large magnetic field heterogeneity around the nanoparticle through which water molecules diffuse (Mornet et al. *Journal Materials Chemistry* 2004, 14: 2161-2175). Diffusion induces dephasing of the proton magnetic moments, resulting in $T_2$ shortening (Mornet et al. *Journal Materials Chemistry* 2004, 14: 2161-2175). Increased $T_2$ relaxivity can be observed at a considerable distance from the nanoparticle, since, in contrast to dipolar relaxation, this susceptibility-induced relaxation does not depend on a direct physical contact between protons and the paramagnetic entity. Thus, $T_2$ shortening can be considered a remote effect, whereas $T_1$ shortening process requires a close interaction between the water molecules and the $T_1$-agents.

Flash nano-precipitation, schematically summarized in FIG. 1, is a micromixing process comprising the steps of dissolving a hydrophobic organic compound in a compatible solvent, providing a polymer also dissolved in the solvent or in an aqueous solvent that is an anti-solvent to the organic compound, and rapidly micromixing the organic solution with the anti-solvent. The materials dissolved in the solvent (s), upon mixing in the anti-solvent, supersaturate the mixture and shortly precipitate into a population of unifoitilly sized nanoparticles. The kinetics of the process afford sufficient control to allow the artisan to mix hydrophobic organic compounds with amphiphilic polymers to produce nanoparticles of predictable size and stability (Johnson et al.,*Australian Journal of Chemistry* 2003, 56: 1021-1024). The process has been disclosed and described in U.S. Patent Application Publication No. 2004/0091546 and in International Publication No.: WO 2006/014626, both of which are incorporated herein in their entirety by reference for all purposes.

In some embodiments, the present invention provides a process comprising the steps of dissolving a hydrophobic organic compound in a solvent, dispersing solid inorganic nanoparticles as a colloidal dispersion in that or another solvent, providing a polymer dissolved in that or another solvent (which may be an aqueous solvent that is an anti-solvent to the organic compound), and micromixing the organic solution, the dispersion and the anti-solvent such that polymeric nanoparticles are formed that retain, sterically stabilized therein, the hydrophobic organic compounds and the solid inorganic nanoparticles. Organics, including but not limited to organic fluorescent materials and therapeutic agents such as vitamins, anti-cancer agents, anti-bacterial agents, steroids, or analgesics may be incorporated into the composite nanoparticle. Solid inorganic nanoparticles including but not limited to imaging agents such as iron oxide nanoparticles, gold nanoparticles, gadolinium, and quantum dots may also be incorporated. Because the encapsulating nanoparticles of these embodiments are produced by means of flash nanoprecipitation, the use of surfactants to stabilize the nanoparticulate dispersions therein is unnecessary, uniformity of particle size is intrinsic to the process rather than a consequence of post-process purification, and the loading capacity for hydrophobic components is high.

The process of preparing multicomponent composite nano-particles using a multi-inlet or multi-stream vortex mixer is illustrated in FIG. 1. The co-encapsulation of organic soluble molecules and inorganic colloidal nano-structures is illustrated. Alternatively, a confined impinging jet mixer as described in U.S. Patent Application Publication 2004/0091546 (incorporated herein in its entirety by reference for all purposes) can be employed.

Especially where unequal momentums of the organic and aqueous streams are advantageous, the multi-stream vortex mixer may be more suitable. Utilization of the multi-stream vortex mixer yields added flexibility in solvent selection, loading of multiple active agents and reduction of solvent to anti-solvent ratios. If two (or more) active agents are incompatible together in an otherwise convenient solvent, the two agents can be mixed from two separate solvent streams, and the velocity of each stream can be separately controlled. A constant flow rate can be provided by a syringe pump for each inlet tube using a Harvard Apparatus pump (model number 7023).

An exemplary but non-limiting multi-inlet vortex mixer, made of any rigid material, comprises a generally cylindrical mixing chamber 0.2333 inches in diameter and 0.0571 inches in height. The chamber is defined by a surrounding wall, a first cover or plate sealably disposed in orthogonal relation to the wall and, opposed thereto, a second sealable cover or plate. Four hollow cylindrical inlet tubes, each 0.0443 inches in diameter, penetrate the wall of the mixing chamber tangentially and, preferably, equidistantly, and are in fluid communication with the chamber. A hollow cylindrical outlet tube, 0.052 inches in diameter, has its long axis (approximately 0.5 inches in length) disposed in orthogonal relation to the inlet tubes. The outlet tube sealably penetrates one of the plates centrally and is in fluid communication with the chamber.

In some embodiments, a confined impinging jet mixer is suitable. A constant flow rate is provided by a syringe pump for each inlet tube using a Harvard Apparatus pump (model number 7023). At least one 100 ml glass syringe (SGE Inc.) is connected to each inlet tube. Two solvent streams of fluid are introduced into a mixing vessel through independent inlet tubes having a diameter, d, which can be between about 0.25 mm to about 6 mm but are between about 0.5 mm to about 1.5 mm in diameter for laboratory scale production. The solvent streams are impacted upon each other while being fed at a constant rate from the inlet tube into the mixing vessel. The mixing vessel is a cylindrical chamber with a hemispherical top. The diameter of the mixing vessel, D, is typically between 2.0 mm to about 5.0 mm, but preferably is between about 2.4 mm to about 4.8 mm. The mixing vessel also contains an outlet with a diameter, $\delta$, that can be between about 0.5 mm to about 2.5 mm but is preferably between 1.0 mm to about 2.0 mm. The outlet of the mixer is connected to an 8-inch line of $\frac{1}{8}^{th}$-inch tubing leading out for product collection.

The organic solutes, inorganic nanostructures and amphiphilic copolymers are dissolved, solubilized or dispersed, together or separately, in a water-miscible organic solvent including but not limited to tetrahydrofuran, dimethyl sulfoxide, or ethanol. Other pharmaceutically acceptable water-miscible solvents are listed in U.S. Pat. No. 6,017,948, which is incorporated herein in its entirety by reference for all purposes. In preferred embodiments, the inorganic nanostructures (generally sized between 1 nm to 700 nm) are "pre-formed" or "pre-existing" in the sense that they retain their discrete particulate nature when solubilized (dispersed) in the water-miscible organic phase and continue to retain it after being incorporated into the nanoparticulate product, even if that product simultaneously encapsulates organics. Pre-formed nanostructures are not formed during the nanoprecipitation process but beforehand.

Intense mixing (i.e., the mixing system operates at a Reynolds number>1600) of the organic solvent stream with water or a predominantly aqueous stream in the multi-inlet vortex mixer induces, in milliseconds, highly supersaturated mixtures (a solute "supersaturates" a solvent when the ratio of the concentration of the solute initially in the mixed streams in the mixing chamber to the concentration of the solute at equilibrium in the final solvent mixture is greater than 1). The artisan can readily measure the stream velocities of the inlet streams and the kinematic viscosity of each stream by means well known in the art, and can determine therefrom the Reynolds number for the system, defined as the sum of the stream flow rates times the average density of the fluids therein divided by the diameter of the inlet stream and divided by the average fluid viscosity of the streams. When solutes mixed under these conditions precipitate from a supersaturated state, nanoparticles of uniform size emerge. They are stable and remain dispersed as they leave the outlet tube. Actives captured within the particles also remain stable.

It is well within the skill of the artisan to "tune" the described mixing system to cause it to produce nanoparticles of a size between 1 nm and 10,000 nm (but preferably less than 1000 nm). A method ("dynamic light scattering") for determining sizes of nanoparticles in the context of the relevant embodiments of the invention is set forth below. Thus, the artisan can select a size distribution that covers a fraction of this spectrum by tuning the system through solvent selection, choice of solute concentrations, stream velocities, conditions of temperature and pressure, and "time-scaling" as described in detail below.

The stability of the nanoparticles is also within the artisan's control, principally through the selection of polymers. In preferred embodiments, amphiphilic polymers or polymer systems are used. The relative sizes (molecular weights) of their hydrophilic and hydrophobic domains determines stability. The particles tend toward instability as hydrophobic domains are made smaller. As hydrophilic domains are made smaller, the particles may remain stable internally but, in dispersions, they will tend to aggregate and flocculate.

In polar liquids, charge stabilization (or "electrostatic stabilization") by Coulombic repulsion is effective. In liquid dispersions, ionic groups can adsorb to the surface of a particle to form a charged layer. To maintain electroneutrality, an equal number of counterions with opposite charge will surround the particles and give rise to an overall charge-neutral double layer. The mutual repulsion of these double layers provides stability. Charge stabilization, however, is not effective in media of low dielectric constant (the vast majority of organic solvents and plasticizers) and thus steric stabilization is required to maintain the stability of dispersions of the particles. Steric stabilization of the colloid is achievable via attachment of macromolecules to the surfaces of the particles in the colloid. Although such attachment may be covalent in nature, it is typically adsorptive. That is, the macromolecule behaves as if "anchored" on the particle's surface but appropriate forces can displace the anchor-point to another site on the surface. Steric stabilization would appear to offer several distinct advantages over electrostatic stabilization, namely, relative insensitivity to the presence of electrolytes in the dispersion media, equal efficacy in both aqueous (polar) and nonaqueous (non-polar) environments, and equal efficacy at both high and low solids content.

In recent years, amphiphilic block copolymers have been demonstrated to be effective steric stabilizers of colloids. The amphiphilic nature of the block copolymer evidently allows one block to have a strong affinity for the hydrophobic materials in the core of the particle and serves to anchor the copolymer to the particle surface. The second block is more compatible with the dispersion media and provides a steric barrier towards particle aggregation and flocculation of the colloid.

In some embodiments, the present invention provides a simple process for producing polymer-encapsulated colloidal particles, each one of which itself comprises a stable colloidal dispersion. The encapsulating particle ranges in size, controllably, from about 25 to about 700 nm. Any colloidal particle dispersion of the present invention will have a distribution of particle sizes for a specific sample. The "size" is then denoted by one of the moments or averages of that distribution. This average is calculated by standard dynamic light scattering data analysis software such as CONTIN by Brookhaven Instruments, Long Island, N.Y. Alternatively, the size can be determined as the first cumulant of the distribution as again calculated using commercial dynamic light scattering software (Brookhaven Instruments, Long Island N.Y.). In the discussion that follows, if a single size is given it will be the first cumulant. And if the size distribution is given and an average size is quoted for the distribution it will refer to the light scattering average particle size described below. The process, moreover, affords the opportunity to control the degree of stability and thus the specific performance of products of the process.

In some embodiments, the invention provides a process for preparing composite nanoparticles from amphiphilic copolymers. The composite nanoparticles comprise inorganic particles encapsulated in the composite together with organic molecules as a colloidal dispersion that is capable of maintaining sufficient overall stability to accommodate a variety of post-processing manipulations. These manipulations include affixing targeting or "homing" molecules to the composite particles, and using the composite particles to transport molecules and particles to targets. Such molecules or particles may be incorporated in the composite particle or affixed, bound, or anchored to the surface thereof.

Typically, the stabilizing amphiphilic polymer is a copolymer of a hydrophilic block coupled with a hydrophobic block. Nanoparticles formed by the process of this invention can be foimed with graft, block or random amphiphilic copolymers. These copolymers can have a molecular weight between 1000 g/mole and 50,000 g/mole, or preferably between about 3000 g/mole to about 25,000 g/mole, and more preferably at least 2000 g/mole. Alternatively, the amphiphilic copolymers used in this invention exhibit a water surface tension of at least 50 dynes/cm$^2$ at a concentration of 0.1 wt %.

Examples of suitable hydrophobic blocks in an amphiphilic copolymer include but are not limited to the following: acrylates including methyl acrylate, ethyl acrylate, propyl acrylate, n-butyl acrylate (BA), isobutyl acrylate, 2-ethyl acrylate, and t-butyl acrylate; methacrylates including ethyl methacrylate, n-butyl methacrylate, and isobutyl methacrylate; acrylonitriles; methacrylonitrile; vinyls including vinyl acetate, vinylversatate, vinylpropionate, vinylformamide, vinylacetamide, vinylpyridines, and vinyl-limidazole; aminoalkyls including aminoalkylacrylates, aminoalkylsmethacrylates, and aminoalkyl(meth)acrylamides; styrenes; cellulose acetate phthalate, cellulose acetate succinate, hydroxypropylmethylcellulose phthalate, poly (D,L lactide), poly (D,L-lactide-co-glycolide), poly(glycolide), poly(hydroxybutyrate), poly(alkylcarbonate) and poly(orthoesters), polyesters, poly(hydroxyvaleric acid), polydioxanone, poly(ethylene terephthalate), poly(malic acid), poly(tartronic acid), polyanhydrides, polyphosphazenes, poly(amino acids) and their copolymers (see generally, Illum, L., Davids, S. S. (eds.) *Polymers in Controlled Drug Delivery* Wright, Bristol, 1987; Arshady, J. Controlled Release 17:1-22, 1991; Pitt, Int. J. Phar. 59:173-196, 1990; Holland et al., J. Controlled Release 4:155-0180, 1986); hydrophobic peptide-based polymers and copolymers based on poly(L-amino acids) (Lavasanifar, A., it al., *Advanced Drug Delivery Reviews* (2002) 54:169-190), poly(ethylene-vinyl acetate) ("EVA") copolymers, silicone rubber, polyethylene, polypropylene, polydienes (polybutadiene, polyisoprene and hydrogenated forms of these polymers), maleic anyhydride copolymers of vinyl methylether and other vinyl ethers, polyamides (nylon 6,6), polyurethane, poly(ester urethanes), poly(ether urethanes), poly(ester-urea), Particularly preferred polymeric blocks include poly(ethylenevinyl acetate), poly (D,L-lactic acid) oligomers and polymers, poly (L-lactic acid) oligomers and polymers, poly (glycolic acid), copolymers of lactic acid and glycolic acid, poly (caprolactone), poly (valerolactone), polyanhydrides, copolymers of poly (caprolactone) or poly (lactic acid) For non-biologically related applications particularly preferred polymeric blocks include polystyrene, polyacrylates, and butadienes. Natural products with sufficient hydrophobicity to act as the hydrophobic portion of the amphiphilic polymer include: hydrophobic vitamins (for example vitamin E, vitamin K, and A), carotenoids and retinols(for example beta carotene, astaxanthin, trans and cis retinal, retinoic acid, folic acid, dihydrofolate, retinylacetate, retinyl palmintate), cholecalciferol, calcitriol, hydroxycholcalciferol, ergocalciferol, alpha-tocopherol, alpha-tocopherol acetate, alpha-tocopherol nicotinate, and estradiol. The preferred natural product is vitamin E which can be readily obtained as a vitamin E succinate, which facilitates functionalization to amines and hyroxyls on the active species.

Examples of suitable hydrophilic blocks in an amphiphilic copolymer include but are not limited to the following: carboxylic acids including acrylic acid, methacrylic acid, itaconic acid, and maleic acid; polyoxyethylenes or polyethylene oxide; polyacrylamides and copolymers thereof with dimethylaminoethylmethacrylate, diallyldimethylammonium chloride, vinylbenzylthrimethylammonium chloride, acrylic acid, methacrylic acid, 2-acrylamide-O-2-methylpropan sulfonic acid and styrene sulfonate, polyvinyl pyrrolidone, starches and starch derivatives, dextran and dextran derivatives; polypeptides, such as polylysines, polyarginines, polyglutamic acids; polyhyaluronic acids, alginic acids, polylactides, polyethyleneimines, polyionenes, polyacrylic acids, and polyiminocarboxylates, gelatin, and unsaturated ethylenic mono- or dicarboxylic acids. The particularly preferred hydrophilic blocks are polyethylene oxide and polyhydroxypropyl acrylamide and methacrylamide to prepare neutral blocks since these materials are in currently approved medical applications. To prepare anionic copolymers, acrylic acid and methacrylic acid and polyaspartic acid polymers are especially preferred, to produce cationic amphiphilic copolymers DMAEMA (dimethylaminoethylmethacrylate), polyvinyl pyridine (PVP) or dimethylaminoethylacrylamide (DMAMAM).

Preferably the blocks are either diblock or triblock repeats. Preferably, block copolymers for this invention include blocks of polystyrene, polyethylene, polybutyl acrylate, polybutyl methacrylate, polylactic acid (PLA), polyglutamic acid (PGA) and PLGA copolymers, polycaprolactone, polyacrylic acid, polyoxyethylene and polyacrylamide. A listing of suitable hydrophilic polymers can be found in *Handbook of Water-Soluble Gums and Resins*, R. Davidson, McGraw-Hill (1980).

In graft copolymers, the length of a grafted moiety can vary. Preferably, the grafted segments are alkyl chains of 4 to 18 carbons or equivalent to 2 to 9 ethylene units in length. In addition, the grafting of the polymer backbone can be useful to enhance solvation or nanoparticle stabilization properties. A grafted butyl group on the hydrophobic backbone of a diblock copolymer of a polyethylene and polyethylene glycol should increase the solubility of the polyethylene block. Suitable chemical moieties grafted to the block unit of the copolymer comprise alkyl chains containing species such as amides, imides, phenyl, carboxy, aldehyde or alcohol groups.

The process yields embodiments of the invention that are products characterized by narrow polydispersity and high loading capacity for one or more active agents stably incorporated in the particles. In one embodiment, the invention provides a process wherein a population of hydrophobic pre-existing nanoparticulate constructs, although surrounded by water, do not aggregate into a hydrophobic center, owing to the presence of an amphiphilic copolymer introduced by the mixing process described herein.

In some embodiments, the pre-existing particles are, surface-modified before being mixed with polymer and organic moieties. A suitable but non-limiting method comprises bonding alkyl or aryl phosphonates to the surfaces of such particles as prescribed in commonly assigned U.S. Provisional Patent Application No. 60/951,113, filed on Jul. 20, 2007. A variety of surface-modifications are available, any of which may be selected, provided that the modification improves incorporation into the composite particle, the stability of the composite particle, the desired release properties or the desired targeting properties of the pre-existing particle (including compatibility at the target-site).

The pre-existing particle is dispersed in a solvent at a controlled temperature and pressure. An amphiphilic polymer is dissolved in a solvent capable of mixing with the solvent containing the pre-existing particle, but possessing different solubility characteristics for the amphiphilic polymer. The two solutions are then mixed at a controlled temperature and mixing velocity, causing selective precipitation of at least one portion of the amphiphilic polymer or polymer system while at least one other portion of the same polymer or polymer system remains soluble. In one embodiment, a product of the process comprises particles that have been functionalized by flash precipitation with an amphiphilic copolymer. In one embodiment, the copolymer is a block copolymer. Preferably, the average size of the functionalized particle is within 30% of its pre-process size if single hydrophobic particles are to be coated by the amphiphilic copolymer. The initial size of the functionalized particles can be between 50 nm and 50 µm. In a preferred embodiment, the ratio of pre-existing particle to amphiphilic copolymer is 1:1. If the desired composite nanoparticle is to include a plurality of smaller hydrophobic nanoparticles or hydrophobic nanostructures alone or in combination with hydrophobic soluble compounds, then the size of the resulting composite nanoparticle may be 60% larger to 400 times larger than an individual hydrophobic nanoparticle. Most significant to the stabilization of colloid in the nanoparticles in certain embodiments of the current invention is the attainment of millisecond micromixing, which is especially advantageous for the steric stabilization of sub-micron particles.

Pre-existing particles can be comprised of biologically or organically active compounds or precursors including, but not limited to anti-inflammatories, anti-depressants, anti-oxidants, organic and inorganic pigments and dyes, proteins, water insoluble vitamins, fluorescent probes, agricultural actives or precursors, ceramics, latex, glass, or metal. Additionally, in certain embodiments, the present invention comprises simultaneously encapsulated hydrophobic and/or electrostatically charged pre-formed particles along with a dissolved hydrophobic active agent.

Some illustrative but non-limiting examples are provided herein for the better understanding of embodiments of the present invention. In those examples, particle size is characterized by dynamic light scattering analysis. The particle sizes are determined from the first cumulant fit of the dynamic light scattering correlation function (West et al., 2003.) The first cumulant fit $\Gamma(q)$ is expressed as [2], $$\frac{\Gamma(q)}{q^2} = \frac{\sum_{k=1}^{max} n_k I_k D_k}{\sum_{k=1}^{max} n_k I_k}, \qquad [2]$$

where $I_k$ is the scattering intensity of particle k, $n_k$ is the number of particles of a given size, and $D_k$ is the diffusion coefficient of particle k. The scattering wave vector q is given by $$q = \frac{4\pi n}{\lambda} \sin\left(\frac{\theta}{2}\right), \qquad [3]$$

where n is the refractive index of the solvent, $\lambda$ the wavelength of the incident light, $\theta$ is scattering angle. The first cumulant is related to the diffusion coefficient by, $$\frac{\Gamma(q)}{q^2} = D_0. \qquad [4]$$

For dilute conditions, the Stokes-Einstein relation applies:

$$D_0 = \frac{kT}{6\pi\mu a}, \qquad [5]$$

where $\mu$ is solvent viscosity. Combining Eqns. 2-5, we obtain an expression for the scattering intensity weighted radius of the particles, $\bar{a}$:

$$\frac{6\pi\mu\bar{a}}{kT} = \frac{\sum_{k=1}^{max,\infty} n_k I_k}{\sum_{k=1}^{max,\infty} n_k I_k \frac{kT}{6\pi\mu a_k}} \qquad [6]$$

For the particles in the Rayleigh scattering range, where the size of the particles is much smaller than the wavelength of scattered light, the intensity of scattered light is proportional to the sixth power of the size for each particle.

This leads to the final expression for the diameter obtained by dynamic light scattering measurements:

$$\bar{a} \equiv a_{h[6,5]} = \frac{\sum_{k=1}^{max,\infty} n_k a_k^6}{\sum_{k=1}^{max,\infty} n_k a_k^5}. \qquad [7]$$

Therefore, the $a_{h[6,5]}$ moment of the size distribution is the appropriate moment to calculate from the simulations and to compare with the dynamic light scattering experiments.

Time-scaling. The process depends on tuning three time scales: 1) time to attain homogeneous mixing ($\tau_{mix}$), 2) time for nucleation and growth of the hydrophobic actives ($\tau_{ng}$), and 3) time of block copolymer self assembly ($\tau_{sa}$). The process has a characteristic mixing time in the range of milliseconds at a Reynolds number greater than 1600.

The mixing time is shorter than the timescale for nucleation and growth of dissolved organic solutes ($\tau_{ng}$). By balancing the nucleation and growth times with the block copolymer assembly time, it is possible to block further particle growth and control nanoparticle size. Too rapid polymer self assembly consumes the stabilizer and results in uncontrolled growth, while too rapid nucleation and growth results in largerthan-desired particle sizes. The average nanoparticle size is thus controlled by the supersaturation levels and kinetics of aggregation of both the block copolymer and hydrophobic compounds.

In one embodiment, the invention provides a composite nanoparticle that encapsulates polymeric colloidal gold (Au) as an imaging contrast agent and β-carotene as a therapeutic. In one embodiment, the invention provides a method of making the composite nanoparticle.

EXPERIMENTAL

EXAMPLE 1

Synthesis of Poly(ethylene glycol-block-caprolactone) Block Copolymer

PEG-b-PCL block copolymers were synthesized by acid catalyzed ring-opening polymerization of ε-caprolactone (PCL) using monomethoxy poly(ethylene glycol) (mPEG) as an initiator according to published procedure (Shibasaki et al., *Macromolecules* 2000, 33:4316-4320). Dichloromethane and PCL were distilled from calcium hydride under reduced pressure shortly before use. Hydrochloric acid in diethyl ether was used as received. mPEG (5000 g/mol) was dissolved in tetrahydrofuran (THF), precipitated into cold hexane, and dried under vacuum. The polymer was further dried by azeotropic distillation of toluene under reduced pressure. To a solution of mPEG in dichloromethane was added PCL. Polymerization was catalyzed by addition of hydrochloric acid solution, and the reaction was carried out at room temperature for 24 h. The copolymer was precipitated into cold hexane, filtered, and dried at room temperature under reduced pressure. In THF at a concentration of 1 mg/ml, the copolymer absorbed no light anywhere in the UV-visible spectrum.

EXAMPLE 2

Synthesis of Hydrophobic Gold Nanoparticles

Dodecanethiol modified gold nanoparticles ($C_{12}$—Au) were prepared by a two-phase reduction of hydrogen tetrachloroaurate ($AuCl_4^-$) in the presence of dodecanethiol according to the method of Brust et al. (*Journal of the Chemical Society-Chemical Communications* 1994, 7:801-802. In brief, an aqueous solution of $AuCl_4^-$ was mixed with a solution of tetraoctylammonium bromide in toluene. The mixture was vigorously stirred and the organic layer separated. Dodecanethiol was added to the organic phase and followed by the addition of aqueous sodium borohydride. The organic phase was separated and evaporated under vacuum. Gold nanoparticles were precipitated into cold ethanol, filtered and dried at room temperature under reduced pressure.

EXAMPLE 3

Preparation of Peg-b-PCL Protected Gold Nanoparticles

A representative synthesis of block copolymer nanoparticles incorporating pre-formed nanostructures prepared via flash nano-precipitation is as follows. To a solution of PEG-b-PCL (5000-b-6000 g/mole) (55 mg) in THF (HPCL grade) (5 ml) was added dry $C_{12}$—Au nanoparticles (8.6 mg). The organic solution was fed (12 ml/min, stream 1), along with water (40 ml/min, streams 2-4), into a four-stream multi-inlet vortex mixer (FIG. 1) using two digitally controlled syringe pumps (Harvard Apparatus, PHD 2000 programmable, Holliston, Mass.), to yield a final solvent composition of 1:10 v/vol % THF:water. The concentrations of $C_{12}$—Au and PEG-b-PCL in final nanoparticle solution were 0.016 wt % and 0.1 wt %, respectively. Nanoparticles were dialyzed against Milli-Q water using a Spectra/Por® dialysis bag with MWCO of 6,000-8,000 (g/mole) (Spectrum Laboratories Inc., California, USA) and stored at room temperature.

EXAMPLE 4

Characterization

Polymer molecular weights and polydispersity indices were measured by gel permeation chromatography (GPC) using a GPC unit (Waters Inc., Milford, Mass.) equipped with a series of Phenogel™ columns and a differential refractive index detector, calibrated with polystyrene standards (Polysciences Inc., Warrington, Pa.). High-resolution $^1$H NMR spectra were obtained using a Varian Inova 400™™ MHz spectrometer.

Nanoparticle size and size distributions were characterized via dynamic light scattering (Brookhaven Instruments, BI-200SM, Holtsville, N.Y.), consisting of double-pumped continuous NdYAG laser (Coherent Inc., wavelength 532 nm, 100 mW, Santa Clara, Calif.), and a photomultiplier with detection angle of 90°. The signal of the photomultiplier was analyzed by autocorrelation (ALV-Laser Vertriebsgesellschaft mbH, ALV-5000/E™, Langen, Germany), yielding the time-averaged scattered average particle size and polydispersity index (PDI). The particle size distribution was calculated using the ALV-5000/E™ software, from the decay-time distribution function with the assumption that the scattering particles behave as hard spheres (Bohren et al, *Absorption and Scattering of Light by Small Particles*, John Wiley, NY, 1983).

UV-visible absorbance spectra of nanoparticles were collected at room temperature using an Evolution 300™ spectrometer (Thermo Electron Inc., Madison, Wis.) in the wavelength range of 200-800 nm, with a resolution of 1 nm. Transmission electron microscopy (TEM) images were obtained on a JOEL 2010™ TEM microscope (Tokyo, Japan) working under an acceleration voltage of 200 kV. For the analysis, a drop of nanoparticles dispersed in water was deposited onto a carbon film supported by a copper grid and dried under reduced pressure. Observations were performed directly following grid preparation.

Figure 2:
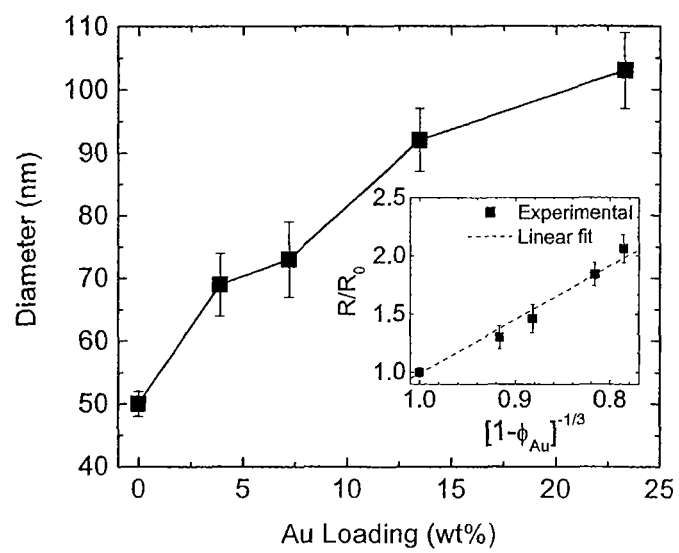
FIG. 2 shows the relationship between the size (hydrodynamic diameter) of PEG-b-PCL-encapsulated ("protected") gold ("Au") nanoparticles and the amount of gold loaded therein. Figure inset demonstrates that size depends on the cubic root of Au volume fraction ($\varphi_{Au}$).
Figure 3:
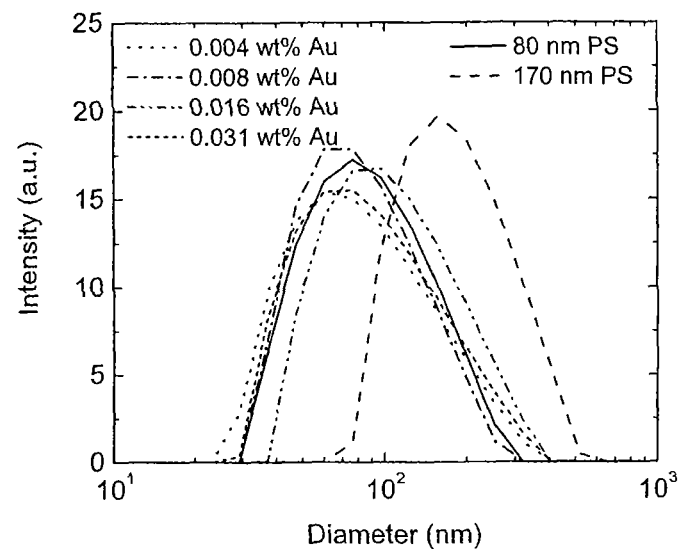
FIG. 3 compares size distributions of PEG-b-PCL protected Au nanoparticless at various Au loadings (in weight percent in final solution), and relative to polystyrene latex spheres.
Figure 11:
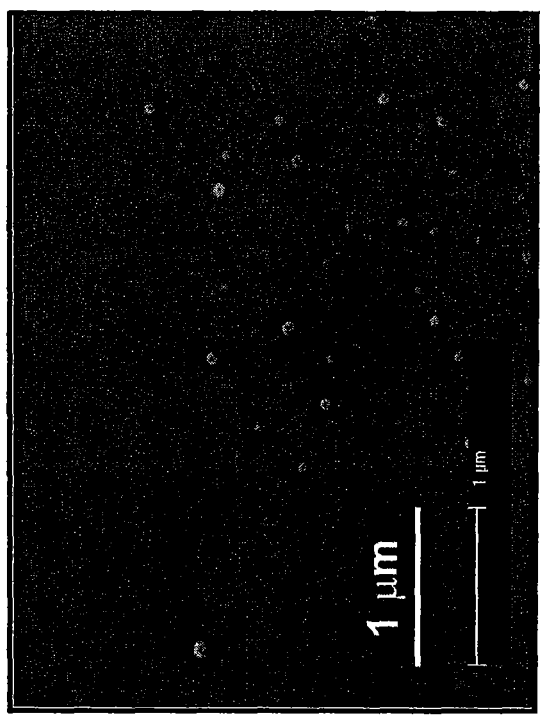
FIG. 11 is scanning electron photomicrograph of representative nanoparticulate products.

Mean particle diameters (hydrodynamic diameters) of PEG-b-PCL-protected Au particles prepared using the multi-inlet vortex mixer as a function of Au nano-particle loading are presented in FIG. 2. The error bars represent the standard deviation in measured diameters of several experimental runs generated at each condition. Nanoparticles were prepared at fixed block copolymer composition (0.1 wt % in the final solution) and Au loading is reported as solids weight percent (Au weight divided by Au and block copolymer weight). The mean size of unfilled polymer nanoparticles as prepared in the multi-inlet vortex mixer is 50±2 nm. Representative nanoparticles loaded at 7.2 wt % Au are shown in a scanning electron microscopic image in FIG. 11. The term 'unfilled' refers to nanoparticles prepared using only the block copolymer stabilizer, and which do not encapsulate any Au colloids. The average nanoparticle diameter is shown to increase with increasing Au concentration, reaching a value of 103±6 nm at a loading of 23 wt % Au. The inset of FIG. 2 shows the nanoparticle radius, R, normalized by the unfilled micelle radius, $R_0$, which scales with the gold colloid volume fraction ($\varphi_{Au}$) as $R/R_0 \propto (1-\varphi_{Au})^{-1/3}$. As elaborated below, the experimentally observed trend is predicted by a reaction model of colloid coagulation in the diffusion limited regime (Fennel-Evans et al., *Advances in Interfacial Engineering Series*, $2^{nd}$ ed. 1999, 417-424). The corresponding particle size distributions, shown in FIG. 3, remain narrow, with PDI values less than 0.25±0.02 obtained in all cases. For reference, particle size distributions of polystyrene calibration standards of similar sizes (80 nm and 170 nm) are also shown in FIG. 3, with measured PDI values of 0.17±0.03 and 0.13±0.03, respectively.

Since no post-synthesis purification of nanoparticle solutions was performed, no material losses are associated with the particle preparation process and high volumetric productivity is achieved. Typical precipitation processes operate at concentrations below 0.05 mg/ml (Kim et al., *Langmuir* 2007, 23:2198-2202) of the block copolymer stabilizer and often require post processing purification for the removal of macroscopic aggregates, resulting in significant material losses and reduced colloid loadings, on average less than 10 wt % with respect to the block copolymer (Nasongkla et al., 2006). Using the multi-inlet vortex mixer, nanoparticles with Au loadings of greater than 20 wt % have been prepared at block copolymer concentrations in the range of 1.0-4.0 mg/mL, demonstrating both enhanced nanoparticle loading capacity and improved volumetric productivity.

Figure 4:
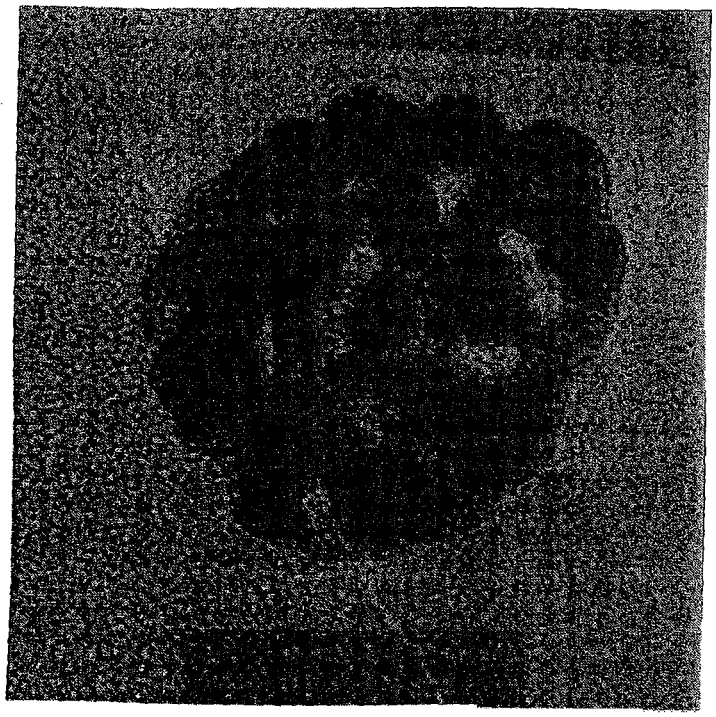
FIG. 4 is a transmission electron micrograph of PEG-b-PCL (5,000-b-6,000 g/mol)-protected Au nanoparticles prepared at a loading of 23.3 wt % Au.

A representative TEM micrograph of PEG-b-PCL-protected Au nanoparticles is shown in FIG. 4. Contrast in the TEM image is provided only by the Au, as the block copolymer is unstained. Individual Au monomers, approximately 5 nm in diameter, are clearly visible. The random, close packing of the Au monomers within the particle core is evident. For a representative Au loading of 23.3 wt %, nearly spherical particles with a mean diameter of 103±6 nm, as determined by dynamic light scattering, are produced. Particle size and size distributions, as determined by dynamic light scattering, are in good agreement with TEM and SEM observations.

EXAMPLE 5

Simultaneous Loading

The flash nanoprecipitation technology was used to simultaneously load hydrophobic organic actives and inorganic colloids for integrated drug delivery and imaging applications. The vitamin A precursor β-carotene was selected as a model hydrophobic compound and encapsulated, in conjunction with Au, within the cores of PEG-b-PCL nanoparticles using the multi-inlet vortex mixer as described. Using ratios of β-carotene:Au:block-copolymer of 30.5:5.0:64.5 wt % (fractional weight of β-carotene, Au, and block copolymer with respect to total solids mass), composite nanoparticles approximately 80 nm in diameter were prepared. To confirm capture of components within the nanoparticle interiors, an as-prepared nanoparticle solution was filtered through a 10K OMEGA™ nanoseparation centrifuge filter membrane (Pall Corporation, East Hills, N.Y.), which allows for the retention of composite nanoparticles on the membrane surface and permits passage of free β-carotene and unprotected Au colloidal particles.

Figure 5:
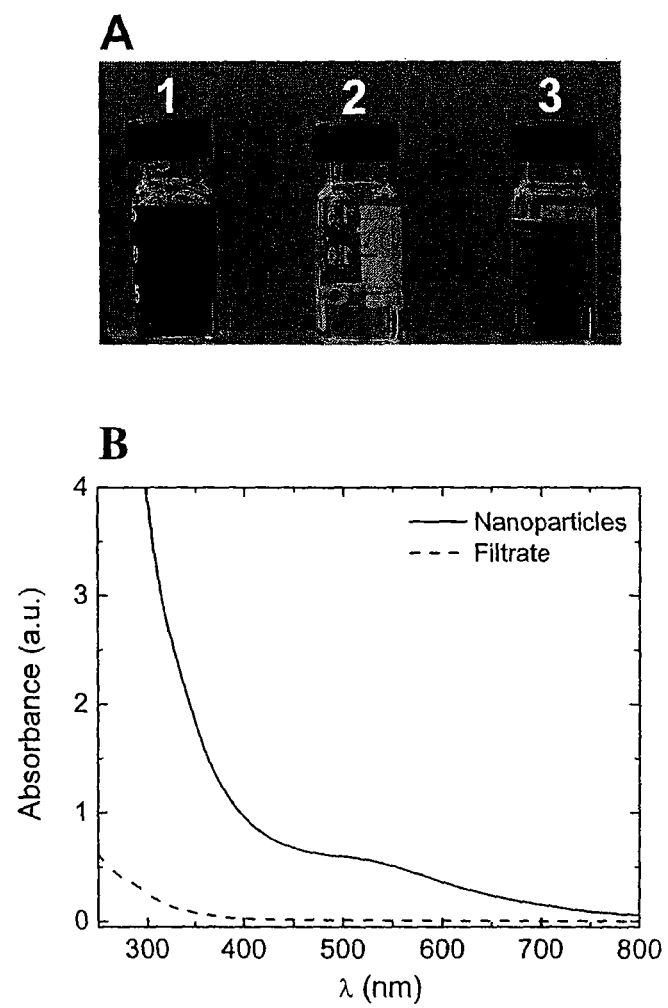
FIG. 5A is a photograph of aqueous dispersions of PEG-b-PCL (5,000-b-6,000 g/mol) nanoparticles encapsulating Au (9.4 wt %) and β-carotene (30.2 wt %), prepared via flash nanoprecipitation (vials 1 and 2) compared with an ordinary (unprotected) gold colloid (vial 3). Vial (1) contains an unfiltered dispersion, vials (2) and (3) contain filtered dispersions.
FIG. 5B compares the light absorption spectra of the dispersions in vials (1) and (2).

The encapsulation of Au monomers (9.4 wt %) and β-carotene (30.2 wt %) within composite nanoparticles prepared by flash nanoprecipitation was first examined visually as shown in FIG. 5A. The composite nanoparticle solution prior to filtration was deep red (vial 1), whereas the filtrate (after filtration via a 10,000 MW ultrafiltration membrane) was clear (vial 2). Complete capture of Au and β-carotene is indicated by transparency of the supernatant (vial 2) when compared to a solution of non-protected Au colloid suspended in THF filtered via the same membrane (vial 3). Total recovery of unprotected Au colloid through the nanoseparation filter (vial 3) was confirmed independently via UV-visible absorbance measurements at 520 nm, where Au colloids of this size exhibit a maximum in the absorbance spectrum. Transfer of β-carotene through the filter was expected based on the molecular weight of the molecule (536.9 g/mol).

Corresponding UV-visible absorption spectra of the composite nanoparticle solution and filtrate are shown in FIG. 5B. A distinct absorbance peak at 520 nm resulting from the presence of Au colloids is seen in the spectrum of the composite nanoparticle solution, whereas this peak is essentially undetected in the solution following filtration. Quantification of Au concentration in the composite nanoparticle and filtrate solutions was made based on calibrated measurements of absorbance values at 520 nm. The UV-visible spectrum of β-carotene does not interfere with that of Au in the wavelength range of 400-800 nm, and thus the absorbance value at 520 nm can be utilized to calculate Au concentration in the composite nanoparticle formulation. Based on this calibration, an Au encapsulation efficiency in excess of 99.5 weight percent was estimated.

The quantification of β-carotene composite nanoparticle loading is complicated by the overlap in absorption spectra of the two components in the UV region, where solutions of β-carotene exhibit an absorbance maximum at 290 nm. As such, we have alternatively prepared PEG-b-PCL nanoparticles in which β-carotene is independently encapsulated. Nanoparticles were isolated as previously described, and the concentration of free β-carotene in the filtrate measured. Based on UV calibration at 290 nm, a β-carotene concentration of approximately 0.05 mg/mL was estimated. This concentration corresponds to the solubility limit of β-carotene in the final solvent composition of 1:10 v/v % THF:$H_2O$. Thus, all β-carotene in excess of the solubility limit was incorporated within the nanoparticles. Because nanoparticle loading relies on compound solubility, the encapsulation efficiency of organic molecules will remain unaffected in multiple component formulations.

While the Applicants will not be bound by any particular theory as to the mechanisms by which any embodiment of the invention works, it is believed that the ability of this technology to provide quantitative homogeneous incorporation of actives arises from the very high level of supersaturation of all components, leading to rapid aggregation and controlled adsorption of the stabilizing polymer on the composite nanoparticle surface (Brick et al., *Langmuir* 2003, 19:6367-6380). The significant advantage of the process is that component loadings can be accurately specified a priori, in contrast to slow, quasi-equilibrium formation processes which lead to unequal incorporation of individual components depending on their solubilities. In our process, drug and imaging agent loadings can be optimized independently and subsequently formulated into a single multifunctional delivery vehicle.

EXAMPLE 6

Stability

Figure 6:
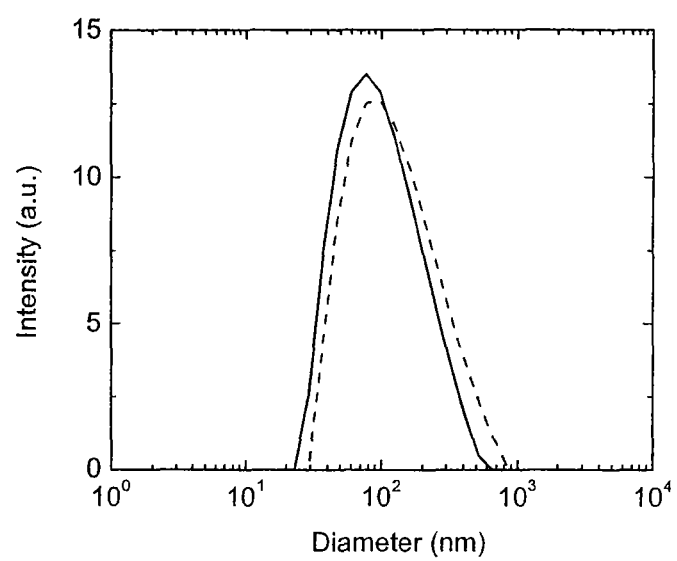
FIG. 6 compares particle size distributions of freshly made PEG-b-PCL (5,000-b-6,000 g/mol) nanoparticles encapsulating Au (9.4 wt %) and β-carotene (30.2 wt %) in 155 mM NaCl (solid line) and nanoparticles stored 28 days (dashed line) at room temperature.

The extended stability of these particles in the presence of physiological salt concentrations was also investigated. Particle size distributions, determined by dynamic light scattering, of PEG-b-PCL (5,000-b-6,000 g/mol) nanoparticles encapsulating Au (9.4 wt %) and β-carotene (30.2 wt %) were stable over time. FIG. 6 shows particle size distributions of PEG-b-PCL-protected β-carotene/Au composite nanoparticles immediately after preparation and dialysis and after one month of storage in 155 mM saline at room temperature. The mean particle diameter and size distribution of the unfiltered solutions increased to a minor extent from approximately 85 nm to 100 nm over this time, indicating particle stability in aqueous environments for extended time periods. The slight increase in particle diameter arises from Ostwald ripening inherent in all nanometer scale particles (Liu et al., *Physical Review Letters* 2007, 98(3))

Figure 7:
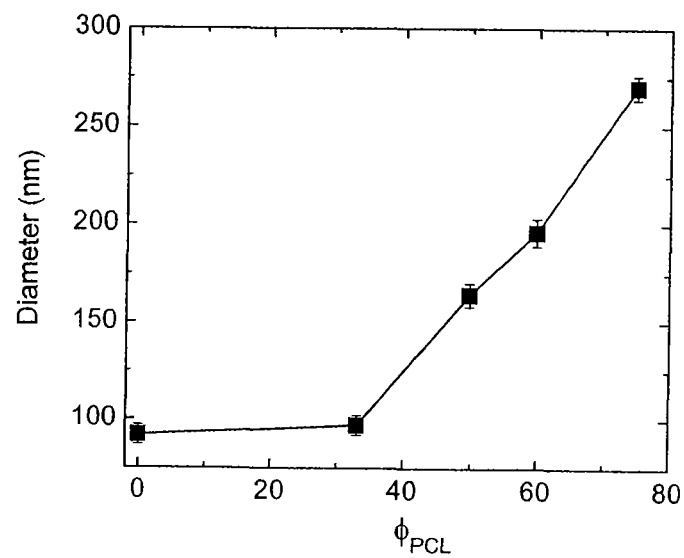
FIG. 7 shows that increasing amounts of the encapsulating polymer in a PEG-b-PCL-protected Au nanoparticle do not add to the size of the particle until the polymer component accounts for more than about 33% of the particle's volume.

Nanoparticles in the size range of 100-300 nm are specifically of interest, as they have been exploited for passive delivery of anti-cancer agents to solid tumor vasculature, where defective vascular architecture and impaired lymphatic drainage allow for improved particle uptake and localization through the enhanced permeation and retention (EPR) effect (Duncan et al., *Annals of Oncology* 1998, 9: 39). We demonstrate the ability to control the size of composite nanoparticles within the above specified range in a predictable fashion in FIG. 7.

PEG-b-PCL-protected Au composite nanoparticles in which the particle size was 'tuned' through addition of an inert component, homopolymer PCL (3,200 g/mol), were prepared. For fixed colloid concentration (0.016 wt % in solution), composite nanoparticle size in the range of 75-275 nm is shown to be a nearly linear function of homopolymer volume fraction ($\varphi_{PCL}$) for PCL loadings above 33 vol %. While Applicants will not be bound by any mechanistic explanation of why any embodiment of the invention works, the relatively constant nanoparticle size with PCL addition for volume fractions below this value is speculated to result from initial filling of the interstitial voids created by the random packing of Au monomers in the nanoparticle core, estimated at approximately 37 vol % (Torquato et al., *Physical Review Letters* 2000, 84:2064-2067). The dense, random nature of monomer packing is supported by TEM imaging as shown in FIG. 4. PCL addition beyond this point contributes to increasing particle diameters. Nanoparticle size and active loading can thus be specified independently of one another, yielding a highly flexible nanoparticle formation platform.

EXAMPLE 7

Prediction of Encapsulated Colloidal Particle Number and Nanoparticle Size

In FIG. 2, the size of polymer-protected Au nanoparticles was shown to be a function of colloidal particle concentration. In this Example, we illustrate that this behavior is well predicted using a simple representation of colloid self-assembly in the diffusion limited regime, as outlined by Fennell-Evans and Wennerstrom. In this model, a system of spherical particles each of uniform radius R undergoing Brownian motion is considered. The spheres are assumed to interact according to a square well potential of infinite energy with an interaction distance of 2 R. At steady state and in the diffusion limited regime, the rate constant for colloid association is shown to be independent of aggregate size and can be used universally to ascertain the kinetics of aggregation, yielding the following general solution to the aggregation process:

$$[P_N] = [P]_0^{tot}\left(\frac{t}{\tau}\right)^{N-1}\left(1+\frac{t}{\tau}\right)^{-N-1}, \quad [8]$$

where $P_N$ is the concentration of particles each composed of N monomers, $[P]_0^{tot}$ is the monomer concentration at t=0, and $\tau=2(k[P]_0^{tot})$, where k is the universal rate constant given by:

$$k \equiv \frac{8}{3}\frac{k_B T}{\mu} \quad [9]$$

for which, $k_B$ is the Boltzmann constant, T is the solution temperature, and μ is the solvent viscosity.

Figure 8:
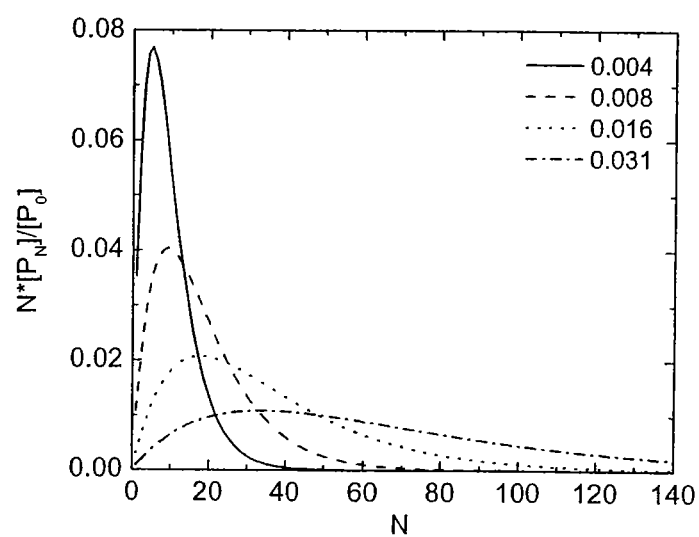
FIG. 8 shows, for various concentrations of gold in solution, the size distribution of gold aggregates in the flash nanoprecipitation product (as formed in about 40 milliseconds), where the "size" of an aggregate is determined by the number of gold monomers in the aggregate.

In the multi-inlet vortex mixer, rapid micromixing in the range of milliseconds is attained, yielding a homogeneous system in which colloid aggregation and block copolymer precipitation occur in the diffusion limited regime. In this manner, colloid aggregation persists until block copolymer deposition on the assembly surface limits further coagulation. Thus, the time allowed for colloid assembly will be dictated by the sum of the characteristic mixing time in the multi-inlet vortex mixer and the block copolymer induction time. In the case of PEG-b-PCL, the copolymer self assembly time is estimated based on a value for comparable molecular weight poly(ethylene glycol)-b-poly(styrene) (1,000-b-3,000 g/mol) block copolymers as reported in literature, where the induction time is approximated to be 37 ms (Johnson et al., 2003). Accounting for an estimated mixing time of 3 ms (Liu et al., *Chemical Engineering Research* 2007) in the multi-inlet vortex mixer, snapshots of the particle size distributions at a time of 40 ms are calculated using Eq. 8 for varying colloid concentrations (wt % in solution). The results of these calculations are shown in FIG. 8. For a given initial monomer concentration $[P_0]$, the final distribution of aggregates, each composed of N monomers, at an assembly time of 40 ms is calculated. The normalized fraction of monomers participating in an aggregate, $N^*[P_N]/[P_0]$, is shown to reach a maximum for each colloid concentration studied, with a shift towards larger maximum values as the colloid concentration is increased. The model additionally predicts a corresponding increase in cluster distribution dispersity as the colloid loading is increased. This trend is supported experimentally, as evidenced by the slightly increasing PDI values of PEG-b-PCL protected Au nanoparticles with increasing Au content shown in FIG. 3.

Model predictions of cluster sizes calculated at t=40 ms were compared to particle diameter values, as determined by dynamic light scattering, for PEG-b-PCL protected Au nanoparticles prepared in the multi-inlet vortex mixer. For particles in the Rayleigh scattering range, the intensity of scattered light is proportional to the sixth power of the size for each particle (Bohren et al., 1983). This leads to the following expression for particle radius as obtained by dynamic light scattering measurements:

$$\overline{R} \equiv R_{6-5} = \frac{\sum_{N=1}^{max,\infty} n_N R_N^6}{\sum_{N=1}^{max,\infty} n_N R_N^5} \quad [10]$$

where $n_N$ is the number of particles of a given radius $R_N$. For a given colloid concentration, particle size can be calculated analytically using Eq. 10 in conjunction with the particle size distributions, $[P_N]$, calculated from Eq. 8. Calculation of nanoparticle core volume was made assuming each $C_{12}$—Au monomer occupies a radius of 4 nm (2.5 nm for Au core and 1.5 nm for $C_{12}$ extended chain length). Additionally, packing of the monomers within the nanoparticle core is assumed to be close packed and random in nature, occupying a volume fraction of 0.63. To account for the PEG-b-PCL stabilizing copolymer, the diameter of unloaded PEG-b-PCL nanoparticles prepared using the multi-inlet vortex mixer (50 nm) was added to the cluster diameters computed through the model.

TABLE 1

Calculated vs. experimental size of block copolymer protected Au NPs prepared via Flash Nanoprecipitation.

| Au concentration | Calculated average diameter ($D_{6-5}$) of PEG-b-PCL protected Au NPs with σ in value reported uncertainty | Experimental diameter of PEG-b-PCL protected Au NPs as determined by DLS | Calculated average number of Au monomers ($N_{6-5}$) in PEG-b-PCL protected Au NPs with σ in value reported as uncertainty |
|---|---|---|---|
| 0.004 wt % | 81 ± 3 nm | 69 ± 5 nm | 38 ± 2 |
| 0.008 wt % | 89 ± 3 nm | 73 ± 6 nm | 70 ± 3 |
| 0.016 wt % | 98 ± 3 nm | 92 ± 5 nm | 109 ± 5 |
| 0.031 wt % | 105 ± 2 nm | 103 ± 6 nm | 126 ± 5 |

Au concentration in column one is reported as weight fraction of Au in solution. The standard deviations (σ) in calculated and experimentally determined values, rounded to the nearest integer, are reported as error.

Calculated cluster diameters as a function of colloid concentration are reported in Table 1 (column 2). The standard deviation in particle size calculated from simulations at each Au concentration is reported as the uncertainties. When compared to experimentally determined particle diameters, as obtained by dynamic light scattering (column 3), the results show that particle size was well predicted using this simple model of colloid aggregation. The model also allows for the prediction of colloid number density within the nanoparticle core. The intensity averaged particle aggregation number, $N_{6-5}$ was similarly calculated according to Eq. 10 and the results shown in Table 1 (column 4). The average aggregation number increased with increasing colloid loading, reaching a 126 (σ=5) for the highest Au concentration investigated. The estimated colloid loading density for this Au composition is well supported by TEM imaging for a similarly prepared sample as shown in FIG. 4. This characterization thus allows for accurate a priori determination of particle size and colloid loading based solely on process inputs, permitting incorporation of multiple inorganic colloidal components at independently specified concentrations.

EXAMPLE 8

Properties of Self Assembled Nanoparticles

Physical properties of colloidal particles are expected to be preserved upon incorporation within the nanoparticle cores. The case of gold colloid encapsulation shown here is particularly interesting owing to the electronic behavior of nanometer sized gold crystals. Gold nanoparticles exhibit localized collective oscillation of surface conduction electrons, leading to distinctive surface plasmon resonance peaks in the UV-visible region (Terrill et al., *Journal of the American Chemical Society* 1995, 117:12537-12548). Since the surface plasmon resonance frequency of a particular sample of gold colloid depends strongly on the size, shape, dielectric properties, and aggregation state of the nanoparticles (Link et al., 2000), measuring the phenomenon in encapsulated forms of the colloid is useful in the engineering of gold-containing nanoparticles.

Figure 9:
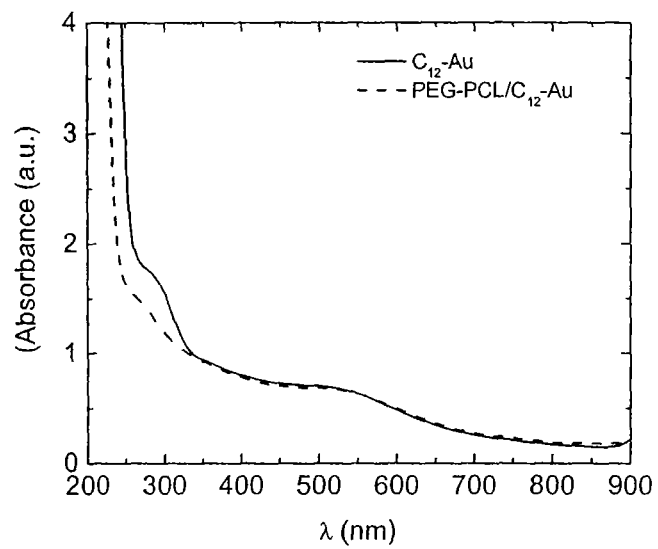
FIG. 9 shows UV-visible absorbance spectra of dodecane capped Au ($C_{12}$—Au) nanoparticles dispersed in THF (solid line) and PEG-b-PCL protected $C_{12}$—Au nanoparticles dispersed in 1:10 v/v THF:water (dashed line).

Encapsulation of Au particles within a block copolymer shell using the multi-inlet vortex mixer was shown to preserve the metallic properties of isolated Au nanoparticles. Although Applicants will not be bound by any theory seeking to explain why embodiments of the invention work, it is thought that when Au particles are in close proximity, they are able to interact electromagnetically, primarily through a dipole-dipole coupling mechanism. This mechanism broadens and red shifts the plasmon resonance bands (Link et al., 2000). FIG. 9 shows the recorded absorbance spectra for dispersions of $C_{12}$—Au in THF and PEG-b-PCL protected $C_{12}$—Au nanoparticles in a THF:water:mixture (1:10 v/vol %). The peak in the extinction spectra, lying at approximately 520 nm, remains unaltered in the nanoparticle assembly, suggesting no overlap in the electronic structure of neighboring Au particles has occurred. The dodecane capping layer dictates the properties surrounding the gold nanoparticle (medium dielectric constant and refractive index), and its thickness, estimated between 1-2 nm (Terrill, et al., 1995), controls the separation distance between neighboring Au monomers, maintaining the particles in an electronically independent state. The interparticle separation distance, and thus electronic properties of the aggregate, can thus be precisely controlled through selection of an appropriate capping ligand.

We have utilized this capacity for control over interparticle distance to generate composite fluorophore-gold assemblies, in which enhanced fluorescence from the organic dye in the nanoparticle assembly is observed. This system is expected to provide a photostable imaging platform with the capacity for particle size control, multi-modal imaging, and reduced toxicity effects.

Figure 10:
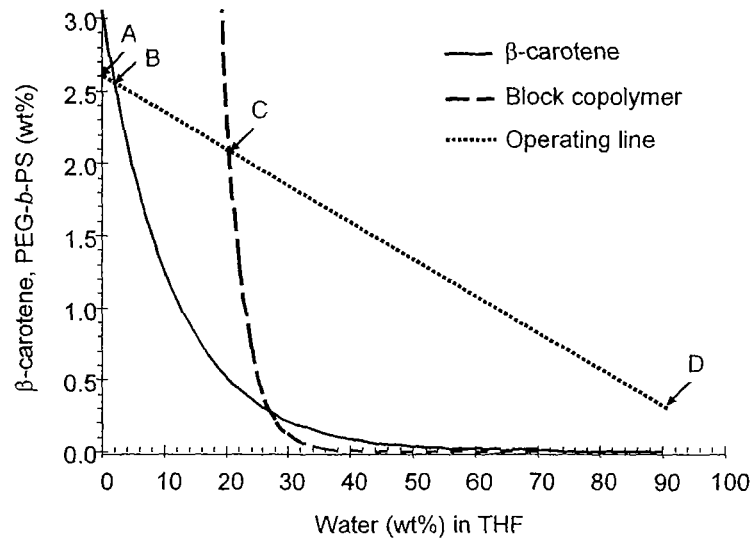
FIG. 10 is a graphical representation of the solubility of β-carotene and a block copolymer stabilizer as a function of THF concentration at 35° C.

Finally, we want to place the process of flash nanoprecipitation we have used here in context with other block copolymer-based nanoparticle formation processes described previously. There are fundamental thermodynamic constraints which limit the ability of processes used by previous researchers (Nasongkla et al., 2006; Yang et al., 2007) to produce multifunctional nanoparticles at high loadings and with controlled particle size. Those limitations can be summarized in FIG. 10, which shows the precipitation concentrations, or solubility boundaries, for two components as a function of anti-solvent addition. Previous researchers have slowly added anti-solvent to initially soluble solutions of block copolymers and imaging agents or drugs (Allen et al., 2000; Kim et al., 2001). FIG. 10 displays the solubility of the organic active β-carotene and the solubility (critical micelle concentration) of a block copolymer stabilizer (poly(ethylene glycol)-block-polystyrene)

as a function of THF content at 35° C. (Johnson, PhD Thesis, Princeton University, 2003). While the solubility data shown in FIG. 10 is specific to PEG-b-PS stabilized β-carotene nanoparticles, as detailed in previous work (Johnson et al., 2003), the operating line shown can be generally applied to describe the flash nanoprecipitation process. The method of slow anti-solvent addition involves traversing the operating line from the initially pure solvent condition (designated A) in which all components are soluble, to the intersection with the solubility curve for β-carotene (designated B) at 2.5 wt % water in THF. At this point β-carotene will begin precipitating. The stabilizing polymer does not start aggregating on the particle surface until the water concentration reaches 23 wt % (designated C). But at this point over 70% of the β-carotene has precipitated as unprotected crystals. Without subscribing to any theory of why embodiments of the invention work, it is thought, in the case of fast mixing, as achieved by the flash nanoprecipitation process (Johnson et al., AICHE Journal 2003, 49:2264-2282), such high levels of supersaturation are produced—in milliseconds—that, at the final solvent composition (designated D), all species aggregate by a diffusion limited, non-specific process. The composition of the resulting nanoparticles reflects the stoichiometry of the feeds and no unincorporated material is produced. In this manner, block copolymer nanoparticles at high drug loadings (2.6 wt % PEG-b-PS to 2.6 wt % β-carotene for the case shown) are easily prepared (Johnson et al., 2003).

Example 9

Nanoparticulate PEG-b-PCL-protected cobalt Ferrite as MRI Contrast Agent

A. Synthesis: All chemicals were purchased from Sigma-Aldrich (St. Louis, Mo.), and unless otherwise noted, used as received. Water, purified by reverse osmosis, ion-exchange, and filtration (Milli-Q water) was used for particle preparation and dialysis. Oleic acid-stabilized cobalt ferrite ($CoFe_2O_4$) nanocrystals were synthesized by Professor Carlos Rinaldi (University of Puerto Rico, Mayaguez). Monomethoxy-terminated poly(ethylene glycol)-block-poly (ε-caprolactone) (5,000 g/mole-block-9,000 g/mole; PEG5-b-PCL9) copolymer was synthesized by ring-opening polymerization of ε-caprolactone using mPEG-OH as macroinitiator and stannous octoanate (SnOct) as catalyst Shuai et al. Macromolecules 2003, 36: 5751-5759.

Block copolymer stabilized CNPs protectively encapsulating cobalt ferrite ($CoFe_2O_4$) nanocrystals were prepared via Flash NanoPrecipitation in a four-stream multi-inlet vortex mixer (MIVM) according to the following protocol: A stock solution of $CoFe_2O_4$ nanocrytals in hexane (0.3 mL) was dried overnight at room temperature for removal of hexane solvent. The particles were then re-suspended in tetrahydrofuran (THF; 5 mL). To this solution was added PEG5-b-PCL9 (110 mg). The organic solution was fed (12 mL/min, stream 1), along with water (40 mL/min, streams 2-4), into a 4-stream MIVM using two digitally controlled syringe pumps. The outlet stream was collected and a sample of the particle suspension (20 mL) was dialyzed extensively against Milli-Q water (4 L) for 72 h using a Spectra/Por® dialysis bag with MWCO of 6,000-8,000 (g/mole) (Spectrum Laboratories Inc., California, USA) and stored at room temperature. Composite nanoparticle size and size distributions were characterized via dynamic light scattering (DLS). Data were analyzed by the cumulant method to determine the hydrodynamic diameters and particle size polydispersity indices.

Oleic acid-stabilized $CoFe_2O_4$ nanocrystals of approximately 10 nm in diameter were impingement mixed in the presence of PEG5-b-PCL9 diblock copolymer. The concentration of block copolymer in all formulations was fixed, while the concentration of $CoFe_2O_4$ was allowed to vary, corresponding to the generation of CNPs with increasingly higher loading of cobalt ferrite. After mixing, particle suspensions were collected, extensively dialyzed against Milli-Q water, and stored at room temperature. Samples of the particle suspensions were analyzed for particle size and particle size distributions via DLS.

Table 2 provides a summary of PEG5-b-PCL9 protected $CoFe_2O_4$ CNPs prepared in this work. The concentrations of PEG5-b-PCL9 copolymer and $CoFe_2O_4$ in the final CNP suspension are estimated based on material concentrations in the respective inlet streams to the mixer. The concentration of PEG5-b-PCL9 is known precisely (column 2). The Fe concentrations (mM) in the final CNP formulations (column 5) are estimated using the concentration of $CoFe_2O_4$ nanocrystals in the stock suspension used for CNP preparation, estimated as 23.3 mg/mL based on reagent concentrations used for nanostructure synthesis. The concentration of Fe was then based on the 1:2 molar ratio of Co to Fe in $CoFe_2O_4$ nanocrystals. For reference, the volume of stock suspension employed for each CNP formulation is also shown column 3, and can be used to directly calculate the Fe concentration once the ICP assay results are available. Finally, the mass loading of iron within the CNP construct, defined as the mass of Fe to mass of block copolymer, is shown in column 6.

TABLE 2

Compositions of PEG-b-PCL Protected $CoFe_2O_4$ CNPs Prepared via Flash NanoPrecipitation [a]

| Sample | PEG5-b-PCL9 in final CNP suspension (mg/mL) | Stock suspension $CoFe_2O_4$ used for CNP preparation (mL) | Estimated $CoFe_2O_4$ in CNP suspension [b] (mg/mL) | Estimated Fe content in CNP suspension [c] (mM) | Fe mass loading (wt %) [d] |
|---|---|---|---|---|---|
| 1 | 2 | 0.10 | 0.042 | 0.36 | 1.0% |
| 2 | 2 | 0.15 | 0.064 | 0.54 | 1.5% |
| 3 | 2 | 0.30 | 0.13 | 1.1 | 3.0% |
| 4 | 2 | 0.60 | 0.26 | 2.2 | 6.0% |

[a] Composite nanoparticles (CNPs) prepared in using inlet stream flow rate ratios of 1:10 vol/vol % THF:Milli-Q water, corresponding to a total CNP suspension volume of 55 mL.
[b] Concentration of $CoFe_2O4$ in final CNP suspension, based on estimated concentration of 23.3 mg/mL $CoFe_2O_4$ in stock suspension.
[c] Iron (Fe) concentration based on molar ratio of 1:2 cobalt:iron. This value is subject to change pending results of ICP assay.
[d] Ratio of iron mass to mass of block copolymer.

Figure 12:
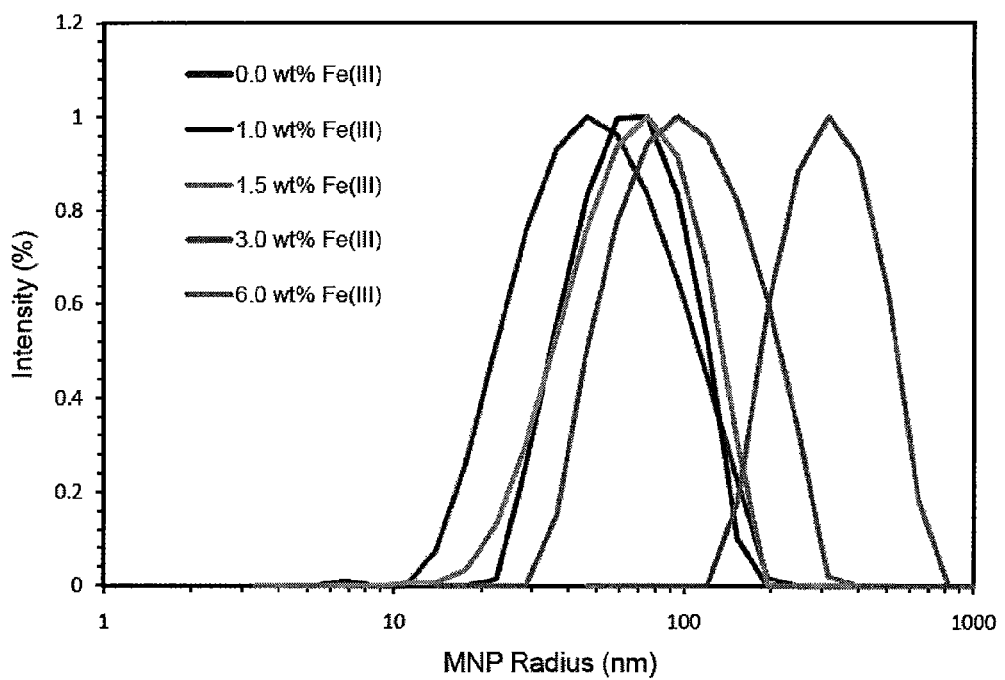
FIG. 12 shows intensity-average particle size distributions, determined by DLS, of PEG5-b-PCL9 protected $CoFe_2O_4$ CNPs prepared via Flash NanoPrecipitation.

The mean intensity-average particle diameters and particle polydispersity indices (PDI) were determined via dynamic light scattering (DLS) using the first and second-order cumulants, respectively, of the intensity distributions. CNP diameters and PDI values for formulations of Table 2 are reported in Table 3, with corresponding particle size distributions shown in FIG. 12. The Fe loading (wt %), defined as the mass ratio Fe:PEG-b-PCL, for each formulation is shown in the legend. As can be seen, the mean intensity-average particle diameter is shown to increase with $CoFe_2O_4$ loading from 86 nm for unloaded PEG5-b-PCL9 particles to 360 nm at the highest $CoFe_2O_4$ loading investigated. In all cases, particle size distributions are unimodal, with PDI values in the range of 0.2-0.25, confirming successful encapsulation of $CoFe_2O_4$ nanostructures.

TABLE 3

PEG-b-PCL Protected $CoFe_2O_4$ CNP Size and Particle Size Polydispersity

| Sample | Mean intensity-average CNP diameter (nm) | CNP particle dispersity index (PDI) |
|---|---|---|
| PEG5-b-PCL9 'unloaded' particles | 86 ± 1 | 0.23 ± 0.02 |
| 1 | 116 ± 2 | 0.21 ± 0.02 |
| 2 | 116 ± 1 | 0.23 ± 0.02 |
| 3 | 175 ± 8 | 0.20 ± 0.02 |
| 4 | 360 ± 10 | 0.24 ± 0.04 |

B. $^1$H-NMR measurements: The NMR was carried out on a Varian Inova-500 NMR spectrometer operating at 500 MHz. For analysis, samples (0.5 mL) of PEG-b-PCL protected $CoFe_2O_4$ CNPs (previously dialyzed against Milli-Q for removal of organic solvent) were filtered via 300 KDa MWCO nanoseparation filters to remove the bulk of liquid (thin film remains on the membrane surface). The retentate was re-suspended in an equal volume (0.5 mL) of deuterium oxide ($D_2O$). Using this stock suspension, a series of samples of increasing dilutions was made using $D_2O$ as diluent. $^1$H-NMR measurements were performed at 25° C. Typically, $T_1$ relaxation times were determined with an Inversion Recovery sequence on 7 time points and $T_2$ relaxation times were measured with a CPMG sequence with echo time varying from 4 ms to 20 ms on 10 points. All data were fitted with a mono-exponential curve. The experimental data were fitted by a least-squares procedure with the expressions:

$$\text{For } T_1: Y_i(t_i) = A(1 - 2\exp(t_i/T_1))$$

$$\text{For } T_2: Y_i(t_i) = A\exp(t_i/T_2) \quad [11]$$

where $t_i$ represent the times at which the magnetization values $Y_i$ was measured. The fitting errors were about 1% determined from computer fitting program.

The longitudinal $T_1$ and transverse $T_2$ relaxation rates were measured on a $^1$H-NMR 500 (500 MHz, 11.75 T, 25° C.). For sample preparation, CNP suspensions in water were concentrated via 300 kDa MWCO centrifuge membrane to approximately 5% initial volume and re-suspended in equal volume $D_2O$ prior to $^1$H-NMR measurements. Confirmation of CNP integrity following centrifugation and re-suspension cycle was obtained via DLS analysis.

Figure 13:
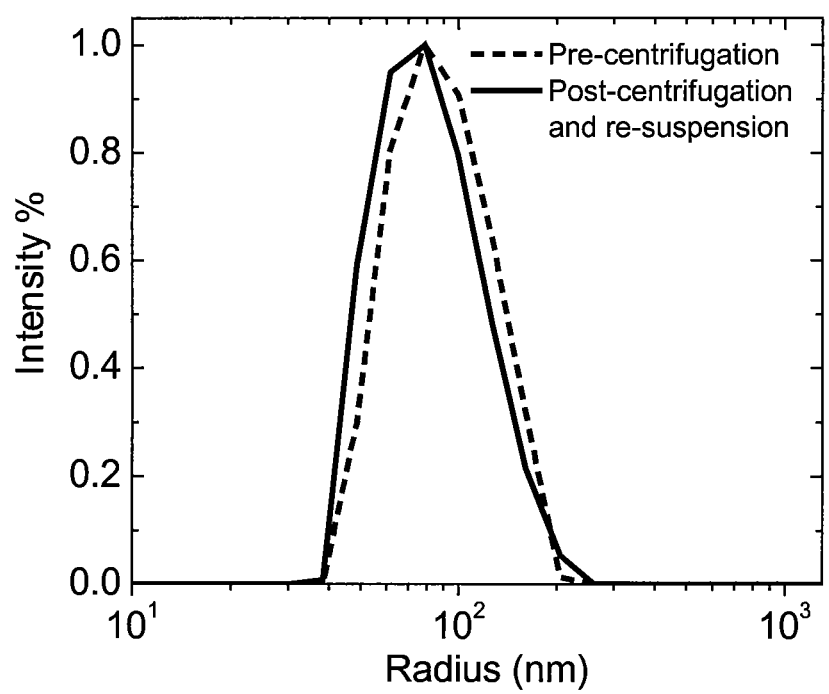
FIG. 13 show DLS spectra of PEG5-b-PCL9 protected $CoFe_2O_4$ CNPs (3 wt % Fe) pre- and post-centrifugation and re-suspension.

As shown in FIG. 13 by the DLS spectra of PEG5-b-PCL9-protected $CoFe_2O_4$ CNPs (3 wt % Fe) pre-centrifugation (dashed line) and post-centrifugation and re-suspension (solid line), the particle size distribution of a representative $CoFe_2O_4$ CNP formulation (3 wt % Fe loading) before concentration (dashed line) and following concentration and re-suspension (solid line) is essentially unchanged, indicating little agglomeration of particles during sample preparation. That is, CNP samples retain their integrity during centrifugation.

Figure 14:
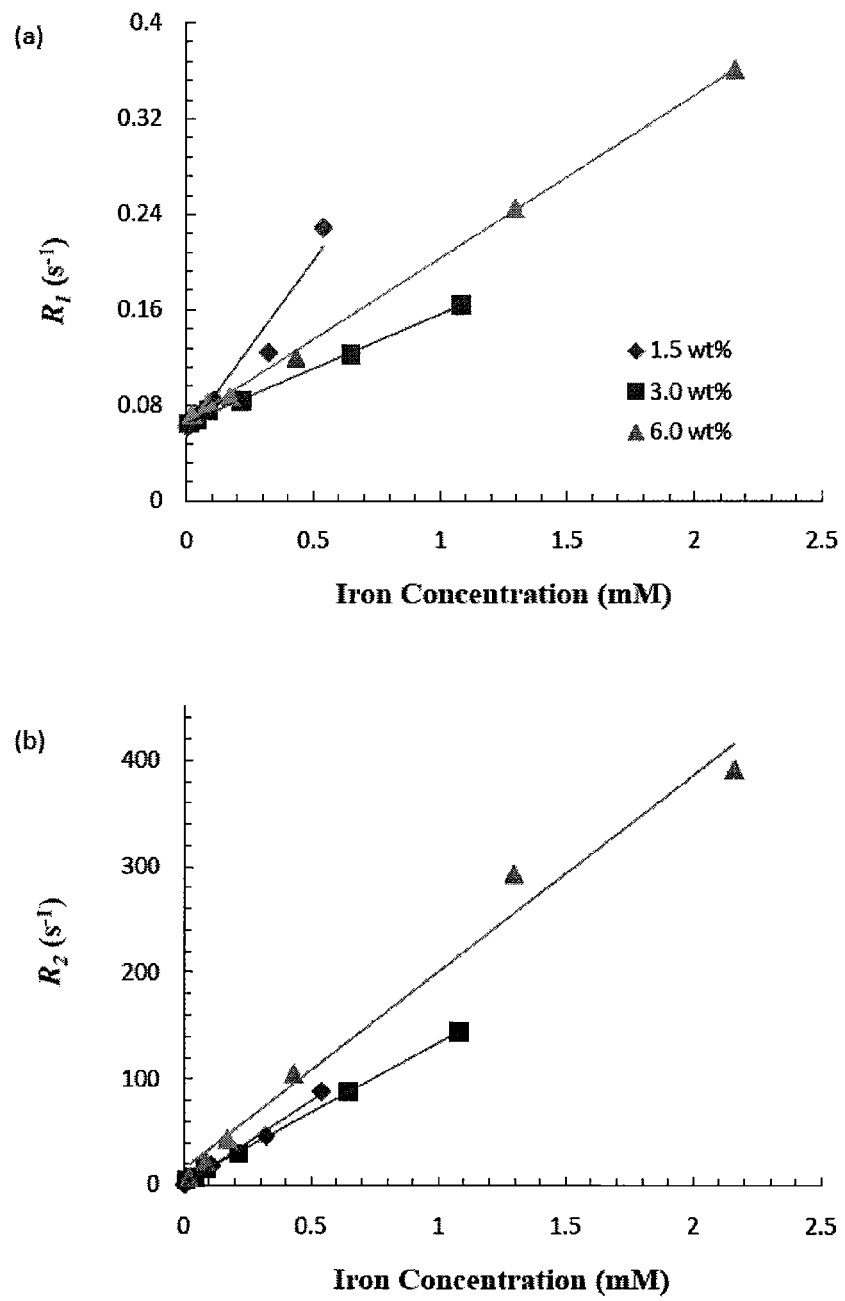
FIG. 14 shows relaxation rates of magnetic moments of protons in water measured at 11.75 T and 25° C. in the presence of PEG5-b-PCL9 protected $CoFe_2O_4$ CNPs.

FIG. 14 shows the relative sensitivity of translational relaxation rate $T_1$ and transverse relaxation rate $T_2$ to the presence of PEG5-b-PCL9 protected $CoFe_2O_4$ CNPs in aqueous media. The Fe loading (wt %) for each CNP formulation, defined as the mass ratio Fe:PEG5-b-PCL9, is shown in the legend. FIG. 14a plots the inverse translational relaxation, $R_1(1/T_1)$. FIG. 14b plots the inverse transverse relaxation, $R_2(1/T_2)$. Relaxation rates were measured at 11.75 T and 25° C. Measurements of the reciprocal relaxation rates $R_1$ and $R_2$ for CNP formulations at various dilutions were used to obtain estimates of the concentration independent relaxivities, $r_1$ and $r_2$. The relaxivity values ($mM^{-1} s^{-1}$) were calculated through the least-squares curve fitting of reciprocal relaxation time versus iron concentration. A summary of results is shown in Table 4.

TABLE 4

Measured $r_1$ and $r_2$ relaxivities for PEG-b-PCL protected $CoFe_2O_4$ CNPs

| Sample | Fe(III) loading | $r_1$ | $R_1^0$ | $r_2$ | $R_2^0$ | $r_2/r_1$ |
|---|---|---|---|---|---|---|
| 1 | 1.5 wt % | 0.29 ± 0.02 | 0.056 ± 0.005 | 158 ± 7 | 0.3 ± 2 | 545 |
| 2 | 3.0 wt % | 0.09 ± 0.01 | 0.065 ± 0.003 | 130 ± 2 | 3 ± 5 | 1444 |
| 3 | 6.0 wt % | 0.12 ± 0.03 | 0.067 ± 0.008 | 195 ± 4 | 16 ± 12 | 1625 |

Uncertainties in values reported are based solely on linear regression fit of data and do not represent reproducibility in experimental measurements. Additional experiments to assess experimental reproducibility are currently under way.

As shown, all CNP formulations have comparable $r_1$ relaxivity values in the range of 0.1-0.25 Fe $mM^{-1}s^{-1}$. These values are significantly smaller than 20-30 Fe $mM^{-1}s^{-1}$ typical of hydrophilic commercially available single nanostructure iron oxide particles encapsulated in dextran matrix, e.g., Clariscan, MION-46 (Ai et al. *Advanced Materials* 2005, 17: 1949—; Wang et al. *European Radiology* 2001, 11: 2319-2331). The reduced accessibility of water to $CoFe_2O_4$ nanocrystals encapsulated within the hydrophobic CNP cores is likely the primary basis for the smaller $r_1$ values obtained in the present case. Because the $T_1$ shortening process requires a close interaction between the water molecules and the $T_1$-agents, it can be inferred that in the present CNP formulations, the interaction of water molecules with $CoFe_2O_4$ nanostructures is restricted to the outer-most layers of $CoFe_2O_4$ nanostructures accessible within the CNP interior.

By contrast, the $r_2$ relaxivities are shown to be quite large. For all $CoFe_2O_4$ CNP formulations examined, the $r_2$ relaxivity values are within the range of 30-100 Fe mM$^{-1}$s$^{-1}$, typical of individual, dextran-coated SPIO particles (Mornet et al. *Journal Materials Chemistry* 2004, 14: 2161-2175; Ai et al. *Advanced Materials* 2005, 17: 1949—; Wang et al. *European Radiology* 2001, 11: 2319-2331). Thus, clustering of the superparamagnetic nanostructures is shown to result in dramatic increases in the r$_2$ relaxivity. The reported values of r$_2$ relaxivities are within the range of other systems which rely on clustering of superparamagnetic nanoparticles to enhance relaxation effects. For example, Ai et al. in *Advanced Materials* 2005, 17: 1949—report comparable r$_2$ relaxivities in the range of 169-471 Fe mM$^{-1}$s$^{-1}$ for PEG5-b-PCL5 micelles encapsulating SPIO particles. The authors correlate increasing r$_2$ relaxivities with increasing Fe micelle loading. However in their case, the increase in Fe loading was an indirect consequence of increasing SPIO particle size (4 nm, 8 nm, and 16 nm) used for micelle preparation. The relaxivity of magnetic nanoparticles has typically been modulated by their core size, which are often in the range of 4-20 nm in diameter, with increasing particle size resulting in higher r$_2$ relaxivity values (Wang et al. *European Radiology* 2001, 11: 2319-2331).

Figure 15:
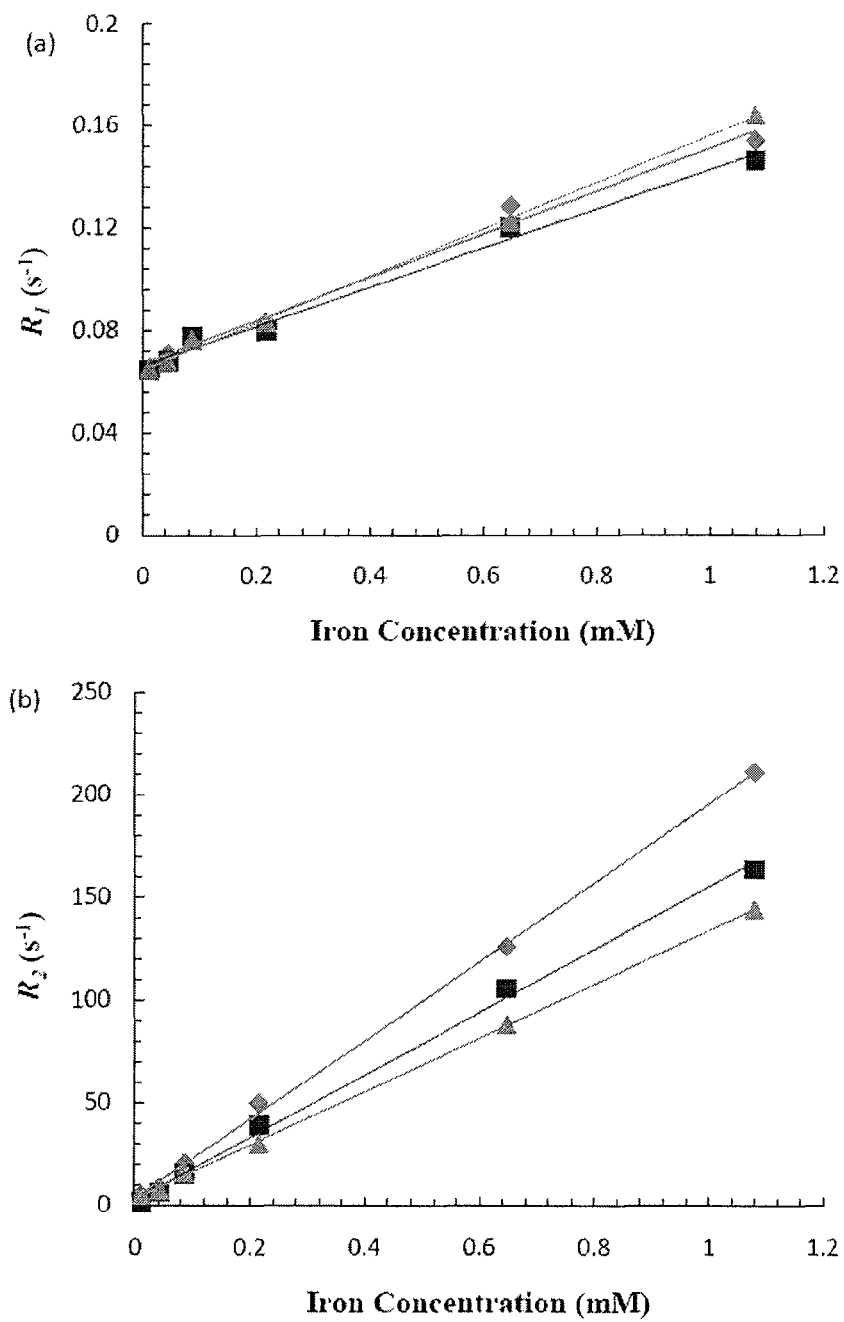
FIG. 15 shows relaxation rates of magnetic moments of protons in water measured at 11.75 T and 298K in the presence of PEG-b-PCL stabilized CoFe2O4 CNPs of identical composition.

PEG-b-PCL protected CoFe2O4 CNPs (3.0 wt % Fe loading) was synthesized on three separate occasions to assess reproducibility. The composition was strictly maintained for each preparation (constant iron and block copolymer loading) and each sample was prepared for NMR analysis. For all three samples, the T$_1$ and T$_2$ relaxation times of each of six separate dilutions (iron concentrations) were measured under identical conditions (11.75 T and 298K). Relaxivity was calculated from relaxation rate and iron concentration data as before. Values for r$_1$ and r$_2$ were obtained from the slope of the least-squares curve fitting of reciprocal relaxation time versus iron concentration for each sample. The y-intercept, R$_{1,2}^0$, represents the inherent relaxation rates of the unloaded PEG-b-PCL particles in the aqueous medium. Values are reported in Table 5, with corresponding plots shown in FIG. 15.

TABLE 5

$^1$H-NMR measured r$_1$ and r$_2$ relaxivities of PEG-b-PCL protected CoFe$_2$O$_4$ CNPs of identical composition.

| Sample | Iron Loading (wt %) | r$_1$(mM$^{-1}$s$^{-1}$) | R$_1^0$(s$^{-1}$) | r$_2$(mM$^{-1}$s$^{-1}$) | R$_2^0$(s$^{-1}$) | r$_2$/r$_1$ |
|---|---|---|---|---|---|---|
| 2 | 3.0 | 0.090 ± 0.01 | 0.065 ± 0.003 | 130 ± 2 | 3.3 ± 4 | 1444 |
| 2' | 3.0 | 0.076 ± 0.04 | 0.067 ± 0.03 | 153 ± 3 | 2.5 ± 4 | 2013 |
| 2" | 3.0 | 0.084 ± 0.07 | 0.067 ± 0.05 | 191 ± 5 | 3.7 ± 5 | 2274 |

Reported uncertainty is the errors based solely on the linear regression fit of relaxation time data and do not represent reproducibility in experimental measurements.

C. Magnetic resonance imaging: The signal contrast enhancement performance of the as-synthesized PEG-b-PCL protected CoFe$_2$O$_4$ CNPs (3.0 wt % Fe, as defined in Table 2) in clinical MR imager (3 T) was additionally investigated. PEG-b-PCL protected CoFe$_2$O$_4$ CNPs were prepared for magnetic resonance imaging (MRI) as follows. A 6 wt % solution of gelatin (from bovine skin, Type B) in water was prepared and poured into an approximately 7"×5" plastic container. The gel was allowed to set overnight at 4° C. Sixteen wells, each approximately 1 cm in diameter, were cut out of the mold. A thin gelatin layer (6 wt %) was then deposited at the bottom of each well and allowed to set overnight at 4° C. As prepared PEG-b-PCL protected CoFe$_2$O$_4$ CNPs in water (following dialysis) were diluted to 60 v %, 40 v %, 20 v %, 10 v %, 6v %, and 2v %. with deionized water. Samples of the CNP suspensions (2 mL) were mixed with gelatin B (120 mg), deposited into individual wells of the prepared gelatin mold. Pure solutions of gelatin B (60 mg/mL) in the absence of CoFe$_2$O$_4$ CNPs were also included for reference. The samples were allowed to set overnight at 4° C. A final layer of gelatin was then placed on the surface and hardened overnight prior to MRI analysis.

Figure 18:
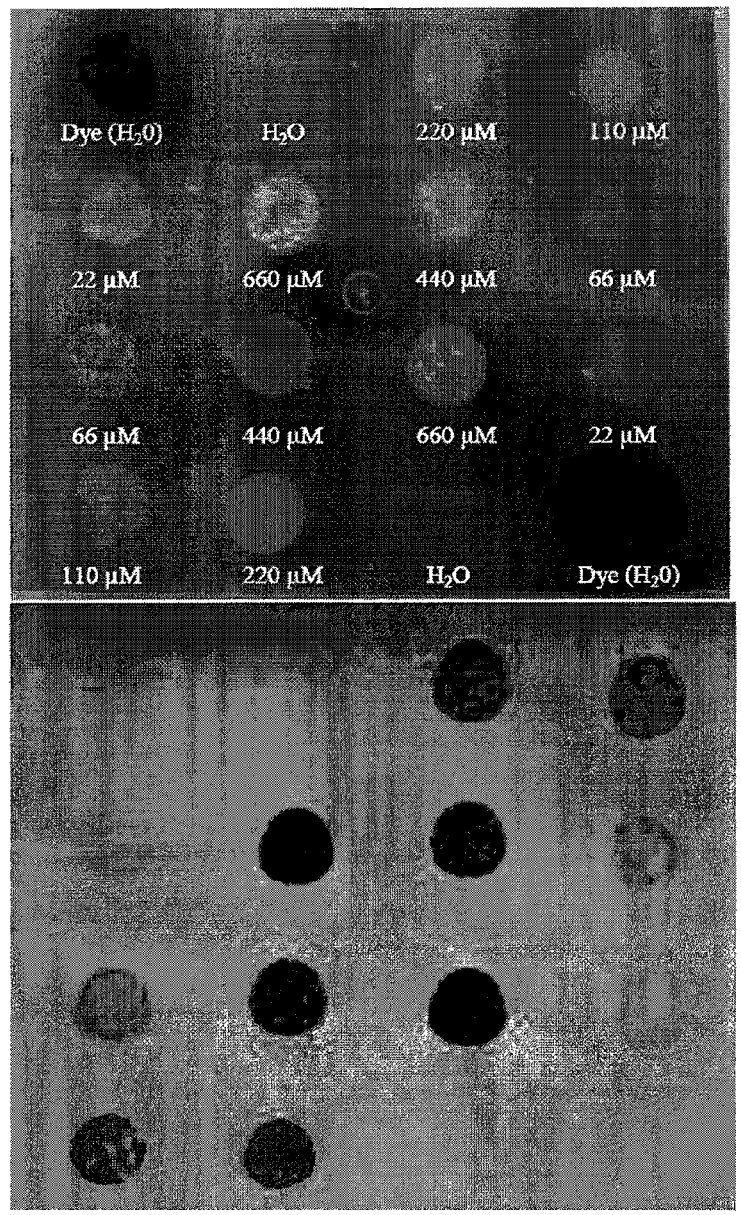
FIG. 18 shows $T_2$-weighted images of PEG5-b-PCL9 protected $CoFe_2O_4$ CNPs prepared at a Fe loading of 3.0 wt %.

FIG. 18*a* is a photographic image of the prepared gel. PEG-b-PCL CoFe$_2$O$_4$ samples are placed in wells, arranged from least concentrated to most concentrated, with Fe concentrations (mM) as indicated on the figure. For identification purposes, a well containing only dye (dissolved in water) is added placed ahead of the CNP samples. The reverse mirror image of the pattern is repeated to assess reproducibility.

Samples were imaged in a 3T clinical magnetic resonance scanner (MAGNETONM Allegra MR system; Siemens, Malvern, Pa.). For T$_2$-weighted imaging, a standard spin-echo pulse sequence was used. The following parameters were adopted: point resolution=0.8×0.8×2 mm, 256×256 bit matrix, five slices with section thickness=2.0 mm, gap spacing=0.2 mm, TE=15 ms, TR=4000 ms, and number of acquisitions=4. Edge and smoothing filter (Siemens) was used for image collection.

As seen in FIG. 18*b*, the PEG-b-PCL protected CoFe$_2$O$_4$ CNPs are highly effective T$_2$ MR contrast agents. At the lowest concentration investigated (27 μM Fe), a clear distinction between samples in the absence of CoFe$_2$O$_4$ CNPs and in their presence can be observed. Thus, the present CNP constructs can be applied for T$_2$-weighted MRI contrast enhancement.

EXAMPLE 10

Co-Encapsulation of Organic Active (Drug) and Colloid Contrast Agent

Composite nanoparticles simultaneously encapsulating an organic active (β-carotene) and an inorganic colloidal contrast agent (CoFe$_2$O$_4$) were prepared via Flash NanoPrecipitation. The final composition of the CNPs (by weight percent of total solids) was 32 wt % β-carotene, 64 wt % PEG-b-PCL and 4 wt % CoFe$_2$O$_4$, corresponding to a Fe(III) composition of 3 wt %. The component compositions of the dually-loaded (CoFe$_2$O$_4$/β-carotene) CNP sample along with the singly-loaded (CoFe$_2$O$_4$) counterpart are summarized below:

| mPEG-b-PCL concentration (mg/mL) | CoFe$_2$O$_4$ concentration, estimated (mg/mL)[b] | β-Carotene concentration (mg/mL) | Fe (III) concentration, estimated (mM)[c] | Fe (III) loading, estimated (wt %)[d] |
|---|---|---|---|---|
| 2 | 0.13 | 0 | 1.1 | 3.0 |
| 2 | 0.13 | 1 | 1.1 | 3.0 |

Figure 16:
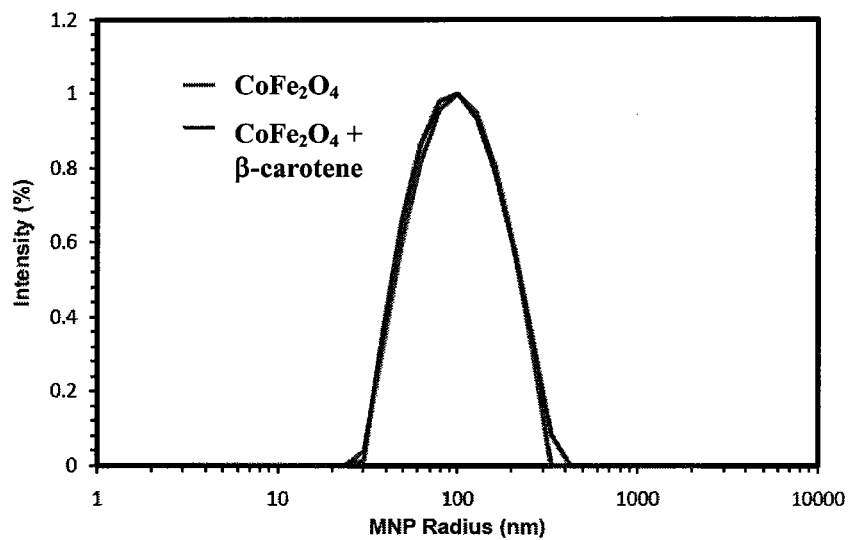
FIG. 16 compares the intensity-average size distributions of PEG-b-PCL protected $CoFe_2O_4$ particles and dually-loaded PEG-b-PCL $CoFe_2O_4$/β-carotene particles.

The intensity-average particle sizes and polydispersity indices (PDI) are reported in Table 6. Uncertainty is reported as the standard deviation in measured diameters and PDI from five separate DLS experimental measurements for each sample. The corresponding intensity average particle size distributions are shown in FIG. 16. Blue diamonds represent CNPs loaded with both CoFe$_2$O4 and β-carotene, while red squares represent CNPs containing only CoFe$_2$O4 colloids. (a) Inverse longitudinal relaxation rates, R$_1$ (1/T$_1$) [s$^{-1}$], and (b) Inverse transverse relaxation rates, R$_2$ (1/T$_2$) [s$^{-1}$], as a function of iron concentration (mM). The iron loading (wt %) for each CNP formulation, defined as the mass ratio of Fe:PEG-b-PCL, is 3.0 wt % for all three samples. Trendlines represent the linear regression fit determined by least-squares curve fitting.

TABLE 6

Particle Size and Polydispersity Indices (PDI) of PEG-b-PCL Protected CoFe$_2$O$_4$ and Dually-loaded PEG-b-PCL CoFe$_2$O$_4$ + β-carotene CNPs

| β-Carotene concentration (mg/mL) | MNP Hydrodynamic Diameter (nm)[a] | MNP polydispersity index, PDI[b] |
|---|---|---|
| 0 | 173 ± 2 | 0.20 ± 0.02 |
| 1 | 173 ± 4 | 0.24 ± 0.01 |

Figure 17:
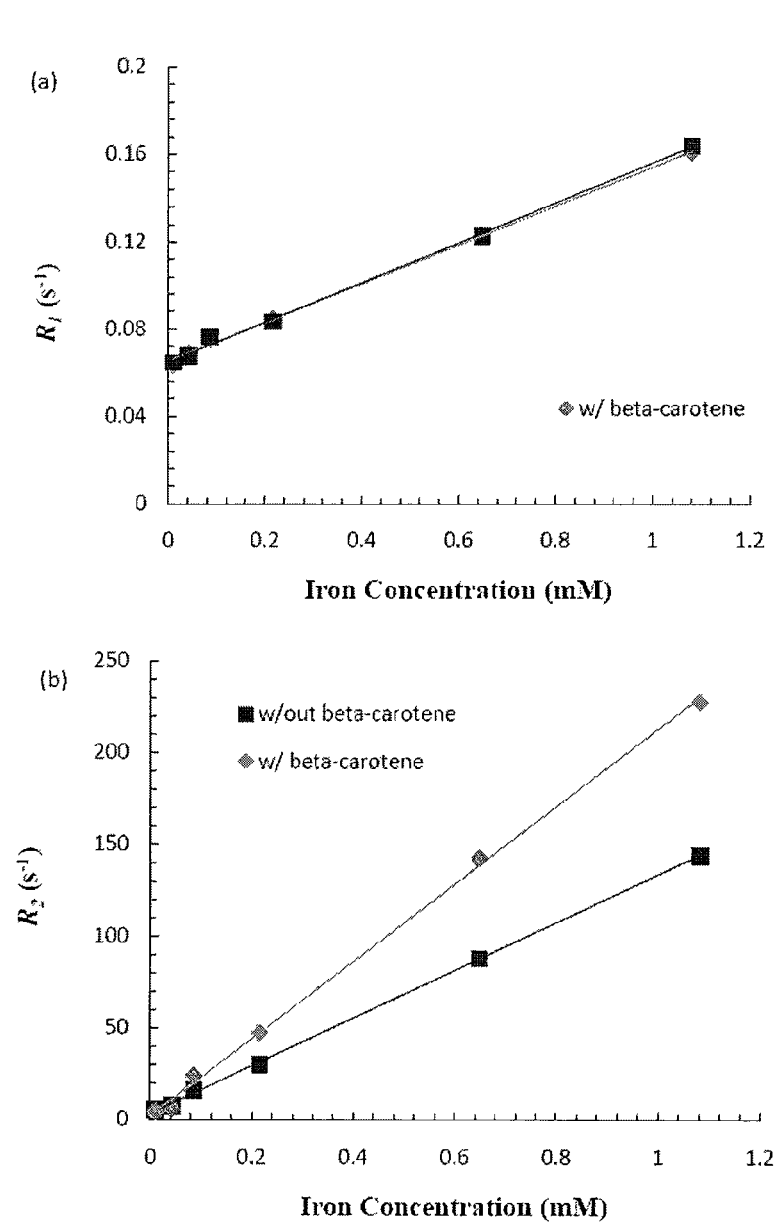
FIG. 17 shows relaxation rates of magnetic moments of protons in water measured at 11.75 T and 298K in the presence of PEG-b-PCL stabilized $CoFe_2$O4 CNPs.

NMR analysis was performed (11.75 T and 298K) to measure T$_1$ and T$_2$ properties of the dually-loaded composite particles. The relaxation rates (R$_1$ and R$_2$) versus iron concentration are displayed in FIG. 17. Blue diamonds represent CNPs loaded with both CoFe$_2$O4 and β-carotene, while red squares represent CNPs containing only CoFe$_2$O4 colloids. (a) Inverse longitudinal relaxation rates, R$_1$ (1/T$_1$) [s$^{-1}$], and (b) Inverse transverse relaxation rates, R$_2$ (1/T$_2$) [s$^{-1}$], as a function of iron concentration (mM). The iron loading (wt %) for each CNP formulation, defined as the mass ratio of Fe:PEG-b-PCL, is 3.0 wt % for all three samples. The relaxatives, r$_1$ and r$_2$, were calculated using a least-squares curve fitting of these data are summarized in Table 7.

TABLE 7

$^1$H NMR measured r$_1$ and r$_2$ relaxivities for PEG-b-PCL nanoparticles singly encapsulating CoFe$_2$O$_4$ colloid or dually encapsulating CoFe$_2$O$_4$

| [B-carotene] (mg/mL) | r$_1$(mM$^{-1}$s$^{-1}$) | R$_1^0$(s$^{-1}$) | r$_2$(mM$^{-1}$s$^{-1}$) | R$_2^0$(s$^{-1}$) | r$_2$/r$_1$ |
|---|---|---|---|---|---|
| 0 | 0.090 ± 0.01 | 0.065 ± 0.003 | 130 ± 2 | 3.3 ± 4 | 1444 |
| 1 | 0.089 ± 0.02 | 0.065 ± 0.002 | 211 ± 4 | 1.8 ± 5 | 2371 |

The CNP iron loading (wt %), defined as the mass ratio of Fe:PEG-b-PCL is 3 wt % for both formulations. Reported uncertainty is the errors associated with the linear regression fit of relaxation time data (FIG. 7) and do not represent represent reproducibility in experimental measurements.

The invention claimed is:

1. A process for manufacturing composite nanoparticles, comprising:
   a. providing;
      i) a first water-miscible organic solvent comprising a hydrophobic organic compound;
      ii) a second water-miscible organic solvent comprising a colloidal dispersion of a plurality of inorganic hydrophobic nanoparticles selected from the group consisting of metallic inorganic hydrophobic nanoparticles and metal oxide inorganic hydrophobic nanoparticles, wherein said inorganic hydrophobic nanoparticles comprise a metallic element;
      iii) a third water-miscible organic solvent comprising an amphiphilic polymer; and
      iv) an anti-solvent; and
   b) micromixing said collodial dispersion of said plurality of inorganic hydrophobic nanoparticles in said second water-miscible organic solvent with said first and third water-miscible organic solvents to create a colloidal composite nanoparticle comprising said metallic element,
      wherein said colloidal composite nanoparticle comprises a plurality of inorganic hydrophobic nanoparticle aggregates;
      wherein said inorganic hydrophobic nanoparticle aggregates comprise a size that is determined by the number of said metallic elements; and
      wherein said collodial composite nanoparticle comprises a hydrophilic shell and said hydrophobic organic compound.

2. The process of claim 1 wherein said hydrophobic organic compound is insoluble in water.

3. The process of claim 1, wherein said first, second and third water-miscible solvents are selected from the group consisting of tetrahydrofuran, dimethyl sulfoxide, and ethanol.

4. The process of claim 1, wherein said anti-solvent comprises water.

5. The process of claim 1, wherein said amphiphilic polymer is selected from the group consisting of a polymer, a copolymer, block copolymer, graft copolymer, comb-graft copolymer, and a random copolymer.

6. The process of claim 1, wherein said inorganic-hydrophobic colloidal particles are surface-modified.

7. The process of claim 6, wherein said surface-modified inorganic hydrophobic colloidal particles comprise an electrostatic charge.

8. The process of claim 1, wherein said hydrophobic organic compound comprises an electrostatic charge.

9. The process of claim 1, wherein said micromixing is performed with a multi-inlet vortex mixer.

10. The process of claim 1, wherein said micromixing is performed with an impinging jet mixer.

11. The process of claim 1, wherein said first, second and third water-miscible organic solvents are the same.

12. The process of claim 1, wherein said first, second and third water-miscible organic solvents are different.

13. The process of claim 1, wherein said micromixing comprises flash-nano precipitation.

14. The process of claim 1, wherein said inorganic hydrophobic nanoparticles are selected from the group consisting of gold particles, palladium particles, magnetic particles, paramagnetic particles, superparamagnetic metals and oxides thereof.

15. The process of claim 1, wherein said inorganic hydrophobic nanoparticles are selected from the group consisting of Gd(III), Mn(II), Mn(III), Cr(II), Cr(III), Cu(II), Fe(III), Pr(III), Nd(III), Sm(III), Tb(III), Yb(III), Ho(III), Eu(II), Eu(III), Er(III), Indium (In), Technetium (Tc), barium particles and quantum dots.

* * * * *